US005837441A

United States Patent [19]

Hjelle et al.

[11] Patent Number: 5,837,441

[45] Date of Patent: Nov. 17, 1998

[54] HANTAVIRUS-ASSOCIATED RESPIRATORY DISTRESS VIRUS ANTIGENS

[75] Inventors: Brian Hjelle; Steve Jenison, both of Albuquerque, N. Mex.

[73] Assignee: University of New Mexico, Albuquerque, N. Mex.

[21] Appl. No.: 210,762

[22] Filed: Mar. 22, 1994

Related U.S. Application Data

[63] Continuation-in-part of Ser. No. 120,096, Sep. 13, 1993, abandoned, and a continuation-in-part of Ser. No. 111,519, Aug. 25, 1993, abandoned, and a continuation-in-part of Ser. No. 141,035, Oct. 26, 1993, abandoned.

[51] Int. Cl.$^{6}$ .......................................................... C12Q 1/70

[52] U.S. Cl. ............................ 435/5; 435/7.92; 435/69.3; 436/518; 530/350

[58] Field of Search ................................ 530/350; 435/5, 435/69.3, 7.92, 97.5; 436/518

[56] References Cited

U.S. PATENT DOCUMENTS 5,298,423 3/1994 Dalrymple et al. .................. 435/320.1

FOREIGN PATENT DOCUMENTS

WO9500648 1/1995 WIPO .

*Primary Examiner*—Marian C. Knode
*Assistant Examiner*—Donna C. Wortman
*Attorney, Agent, or Firm*—Hoffman, Wasson & Gitler

[57] ABSTRACT

The invention provides HARDS virus rDNA for expression in molecular clones. The expressed products are useful in immunodiagnostics, prophylactics, and therapeutics for the HARDS virus and related hantaviruses. Of particular interest are a type-specific epitope of the HARDS virus G1 protein, and dominant epitopes of the HARDS virus N protein cross-reactive with antibodies to the HARDS virus and the related hantavirus PHV, both expressed by cDNA clones according to the invention.

29 Claims, 13 Drawing Sheets

RECOMBINANT ANTIGENS: CONTEMPLATED USES

```
|———— G1 ————|———— G2 ————| HARDS
|———————————————————————————| M SEGMENT
```

1. DESIGN PRIMERS BASED ON RELATED VIRUSES
2. PCR

PCR PRODUCT

CLONE

USE AS Ag IN DIAGNOSTIC TEST

USE AS Ag IN IMMUNIZATIONS AND FOR VACCINES

EXPRESS PROTEIN IN
E. coli,
BACULOVIRUS
OR VACCINIA VIRUS

Ab

TYPE-SPECIFIC IgG SEROREACTIVITY

FIG. 5/A

```
                                                                              1
NMHV                                                                      STLQS
                                                                          *****
PHILL     OOOTSORATTTSAGMSQLRETQEEITRHEQQLVIARQKLKEAERTVEVDPDDVNKSTLQS
                         **:*  :  ************:******:***  ***  ****  *  ***
PUUMALA                  MSDLTDIQEEITRHEQQLVVARQKLKDAERAVEVYPDDVIKNTLQA
                         1       10        20        30        40
consens                  MS+L + QEEITRHEQQLV!ARQKLK+AER VEV PDDV KSTLQS
          1         10        20        30        40        50        60

            10        20        30        40        50        60
NMHV      RRAAVSALETKLGELKRELADLIAAQKLASKPVDPTGIEPDDHLKEKSSLRYGNVLDVNS
          ** *** ** ** * **:*** *  **:  ********* ****** *** *********
PHILL     RRSAVSTLEDKLAEFKRQLADVISRQKMDEKPVDPTGIELDDHLKERSSLQYGNVLDVNS
          *  ** ******::** :** :** *** ** ****** ********** ********
PUUMALA   RQQTVSALEDKLADYKRRMADAVSRKKMDTKPTDPTGIEPDDHLKERSSLRYGNVLDVNA
           50        60        70        80        90        100
consens   RR AVSALEDKLA+%KR+$AD !SRQK$D KPVDPTGIEPDDHLKERSSLRYGNVLDVNS
                   70        80        90        100       110       120

            70        80        90        100       110       120
NMHV      IDLEEPSGQTADWKSIGLYILSFALPIILKALYMLSTRGRQTIKENKGTRIRFKDDSSYE
          ** **********  ** **  ********** *********:****************
PHILL     IDIEEPSGQTADWLKIGSYIIEFALPIILKALHMLSTRGRQTVKENKGTRIRFKDDSSYE
          ************  ** *:* *  ******* *********************** *:*
PUUMALA   IDIEEPSGQTADWYTIGVYVIGFTIPIILKALYMLSTRGRQTVKENKGTRIRFKDDTSFE
           110       120       130       140       150       160
consens   IDIEEPSGQTADW  IG Y!I FALPIILKALYMLSTRGRQT!KENKGTRIRFKDDSS%E
                   130       140       150       160       170       180

            130       140       150       160       170       180
NMHV      EVNGIRKPRHLYVSMPTAQSTMKADEITPGRFRTIACGLFPAQVKARNIISPVMGVIGFS
          :***** * ***************:* ******** *******: **************
PHILL     DVNGIRRPKHLYVSMPTAQSTMKAEELTPGRFRTIVCGLFPAQIMARNIISPVMGVIGFA
          *:*************************************** **  *** *********
PUUMALA   DINGIRRPKHLYVSMPTAQSTMKAEELTPGRFRTIVCGLFPTQIQVRNIMSPVMGVIGFS
           170       180       190       200       210       220
consens   +!NGIRRPKHLYVSMPTAQSTMKA+ELTPGRFRTIVCGLFPAQ! ARNIISPVMGVIGFS
                   190       200       210       220       230       240

            190       200       210                 220       230       240
NMHV      FFVKDWMERIDDFLAARCPFLPEQKDPRDAA.....LATNRAYFITRQLQVDESKVSDIE
          ****** : :  **  ****  : * : *      *  ***  **  **  **:
PHILL     FFVKDWADKVKAFLDQKCPFLKAEPRPGQPAGEAEFLSSIRAYLMNRQAVLDETHLPDID
          ****** :*: *:: *** * * ** ** * ***  * * * ** *** * ***
PUUMALA   FFVKDWPEKIREFMEKECPFIKPEVKPGTPAQEVEFLKRNRVYFMTRQDVLDKNHVADID
           230       240       250       260       270       280
consens   FFVKDW +K! +F$+  CPFLK +  PG+PA E EFL  NRAYFMTRQ VLDE HV DI+
                   250       260       270       280       290       300

                   250       260       270       280       290       300
NMHV      DLIADARAESATIFADIATPHSVWVFACAPDRCPPTALYVAGMPELGAFFAILQDMRNTI
          *:  *    *        ** ************ *:*** ****************
PHILL     ALVELAASGDPTLPDSLENPHAAWVFACAPDRCPPTCIYIAGMAELGAFFAILQDMRNTI
          *:: ******* **    * * ********* ******:********** *********
PUUMALA   KLIDYAASGDPTSPDDIKSPNAPWVFACAPDRSPPTCIYVAGMAELGAFFSILQDMRNTI
           290       300       310       320       330       340
```

FIG. 5/B

```
consens   L!+ AASGDPT PDDI  PHA WVFACAPDRCPPTCIY!AGMAELGAFFAILQDMRNTI
                310        320        330        340        350        360

                310        320        330        340        350   356
NMHV      MASKSVGTSEEKLKKKSAFYQSYLRRTQSMGIQLDQKIIILYMSHWGREAVNHFHL
          **** *** *************************** ** :**  ** * ******
PHILL     MASKTVGTAEEKLKKKSAFYQSYLRRTQSMGIQLDQRIILMYMIEWGNEVVNHFHLGDDM
          ************* ** *********************:** *** * *:********
PUUMALA   MASKTVGTAEEKLKRKSSFYQSYLRRTQSMGIQLDQRIILLYMLEWGKEMVDHFHLGDDM
           350        360        370        380        390        400
consens   MASKTVGTAEEKLKKKSAFYQSYLRRTQSMGIQLDQRIIL$YM EWG E V+HFHLGDDM
                370        380        390        400        410        420

NMHV

PHILL     DPELRQLAQALIDQKVKEISNQEPLKIOOPACIASTFIAYISSCLLOFIITIIIQVIVML
          ***** *** *****************                 *
PUUMALA   DPELRGLAQSLIDQKVKEISNQEPLKIO................L
           410        420        430               435
consens   DPELR LAQ LIDQKVKEISNQEPLKIO                L
                430        440        450        460        470        480

NMHV

PHILL     ISLTNSQLNIALNOHLGTOLMEQYCKTELSLOFISVFIISKATTYLNTLIYMHVAYIOVY

PUUMALA

consens
                490        500        510        520        530        540

NMHV

PHILL     IYYLNSVFSOLLFKEYTT

PUUMALA

consens
                550        558
```

FIG. 6

```
          1        10        20        30        40        50        60
HARDS     GLGQGYVTGSVETTPILLTQVADLKIESSCNFDLHVPATTTQKYNQVDWTKKSSTTESTN
          ***** * * *:  *:     *  ** ******* *     * *       * **  * *
PHILL     GLGQGLVIGTVDLNPVPVESVSTLKLESSCNFDVHTSSATQQAVTKWTWEKKADTAETAK
           ******:* *:*    *:: * *********** *** * **  ****** * * **
PUUMALA   RLGQGLVVGSVELPSLPIQQVETLKLESSCNFDLHTSTAGQQSFTKWTWEIKGDLAENTQ
          1        10        20        30        40        50        60
consens   GLGQGLV!GSV+L P!P!+QV TLKLESSCNFDLHTS ATQQ %TKWTWEKK DTAE T+
          1        10        20        30        40        50        60
                  70        80        90       100       110       120
HARDS     AGATTFEAKTKEINLKGTCNIPPTTFEAAYKSRKTVICYDLACNQTHCLPTVHLIAPVQT
          *  ***: *  * ** * * **     * * * **** **** **** * *** ****: *
PHILL     AASTTFQSKSTELNLRGLCVIPTLVLETANKLRKTVTCYDLSCNQTACIPTVYLIAPIHT
          * ** ** ** * ****** ***** ***   :***: ********* * *****   ** *
PUUMALA   ASSTSFQTKSSEVNLRGLCLIPTLVVETAARMRKTIACYDLSCNQTVCQPTVYLMGPIQT
                  70        80        90       100       110       120
consens   A STTF+ KS E!NLRGLC IPTLV ETA K$RKT! CYDLSCNQT C PTVYLIAP!QT
                  70        80        90       100       110       120
                  130       140       150       160       170
HARDS     CMSVRXYI.GLLSSRIQVIYEKTYCVTGQLIEGLCFIPTHTIALTQPGHTYDXMTLPVTC
          *        **   **** ******* ***:** ** * ** ** ** ****  * ** *
PHILL     CVTTKSCLLGLGTQRIQVTYEKTYCVSGQLVEGTCFNPIHTMALSQPSHTYDIVTIPVRC
          *:******* ** ***** ************* ****************** *  ***
PUUMALA   CITTKSCLLSLGDQRIQVNYEKTYCVSGQLVEGICFNPIHTMALSQPSHTYDIMTMMVRC
                 130       140       150       160       170       180
consens   C!TTKSCLLGLG QRIQV YEKTYCVSGQL!EG CFNPIHTMALSQPSHTYDIMT$PVRC
                 130       140       150       160       170       180
                   190       200       210       220       230
HARDS     FLVAKKL..GTQLKLAVELEKLITGVSCTENSFQGYYICFIGKHSEPLFVPTMEDYRSAE
          * :***        **   : *        **       ***:** *  *** *****:*:*  :
PHILL     FFIAKK.TNDDTLKIEKQFETILEKSGCTAANIKGYYVCFLGATSEPIFVPTMDDFRASQ
          * : ** *   * :****:***   :* **** *   ***:*   *  *** :** :**:*  :
PUUMALA   FLVIKKVTSGDSMKIEKNFETLVQKNGCTANNFQGYYICLIGSSSEPLYVPALDDYRSAE
                 190       200       210       220       230       240
consens   FL!AKK T GD $KIEK+FETL!+K GCTANNFQGYY!CFIG  SEPL%VPT$+D%RSA+
                 190       200       210       220       230       240
          240       250       260       270       280       290
HARDS     LFTRMVLNPRGEDHDPDQNGQGLMRIAGPVTAKVPSTETTETMQGIAFAGAPMYSSFSTL
              *   * *****          ****    * ****  :* **:** * *:* * * *
PHILL     ILSDMAISPHGEDHDSALSSVSTFRIAGKLSGKAPSTESSDTVQGVAFSGHPLYTSLSVL
          :** **  *******       **  *****  **************:**** *****  **
PUUMALA   VLSRMAFAPHGEDHDIEKNAVSAMRIAGKVTGKAPSTESSDTVQGIAFSGSPLYTSTGVL
                 250       260       270       280       290       300
consens   !LSRMA  PHGEDHD + N VS MRIAGKVTGKAPSTESS+TVQG!AFSG P$YTS SVL
                 250       260       270       280       290       300
          300       310       320       330       340       350
HARDS     VRKADPEYVFSPGIIAESNHSVCDKKTVPLTWTGFLAVSGEIEKITGCTVFCTLAGPGAS
            * ** *: ***** * ** ****** ******:*    * *** * **:*********
PHILL     ASKEDPVYIWSPGIIPERNHTVCDKKTLPLTWTGYLPLPGGIEKTTQCTIFCTLAGPGAD
           **:****** **** * **  :*:**********:   *** *******:**********
PUUMALA   TSKDDPVYIWAPGIIMEGNHSICEKKTLPLTWTGFISLPGEIEKTTQCTVFCTLAGPGAD
                 310       320       330       340       350       360
consens    SK+DPVY!WSPGII E NHS!C+KKTLPLTWTG%L LPGEIEKTTQCT!FCTLAGPGAD
                 310       320       330       340       350       360
          360       370       380       390       400    407
HARDS     CEAYSETGIFNISSPTCLVNKVQKFRGSEQRINFMCQRVDQDVVVYCNGQ
          *****:************:* ** *** ** * * ***** *:******
PHILL     CEAYSDTGIFNISSPTCLINRVQRFRGAEQQIKFVCQRVDLDIVVYCNGM
          *****:********************* ***********:** ******
PUUMALA   CEAYSETGIFNISSPTCLINRVQRFRGSEQQIKFVCQRVDMDITVYCNGM
                 370       380       390       400       410
consens   CEAYS+TGIFNISSPTCL!NRVQRFRGSEQQIKFVCQRVD$D!VVYCNGM
                 370       380       390       400       410
```

FIG. 7

SEQ ID NO:18: Complete sequence of insert of p3H226 S 1129 CR-7 clone.
Primers used in its amplification are not included.

```
AGCACATTAC AGAGCAGACG GGCAGCTGTG TCTGCATTGG AGACCAAACT CGGAGAACTC   60
AAGCGGGAAC TGGCTGATCT TATTGCAGCT CAGAAATTGG CTTCAAAACC TGTTGATCCA  120
ACAGGGATTG AACCTGATGA CCATTTAAAG GAAAAATCAT CACTGAGATA TGGAAATGTC  180
CTTGATGTAA ATTCCATTGA CCTAGAAGAA CCAAGTGGGC AAACAGCTGA TTGGAAATCC  240
ATCGGACTCT ACATTCTAAG TTTTGCATTA CCGATTATCC TTAAAGCCTT GTACATGTTA  300
TCTACTAGAG GCCGTCAAAC AATCAAAGAA AACAAGGGAA CAAGAATTCG ATTTAAGGAT  360
GATTCATCTT ATGAAGAAGT CAATGGAATA CGTAAACCAA GACATCTATA TGTTTCTATG  420
CCAACTGCTC AGTCTACAAT GAAAGCAGAT GAGATTACTC CTGGGAGGTT CCGTACAATT  480
GCTTGTGGGT TATTCCCGGC CCAAGTCAAA GCAAGGAATA TTATCAGTCC TGTTATGGGT  540
GTGATTGGCT TTAGTTTCTT TGTGAAAGAT TGGATGGAAA GAATTGATGA CTTTCTGGCT  600
GCACGTTGTC CATTTCTACC CGAACAGAAA GACCCTAGGG ATGCTGCATT GGCAACTAAC  660
AGAGCCTATT TTATAACACG TCAATTACAG GTTGATGAGT CAAAGGTTAG TGATATTGAG  720
GATCTAATTG CTGATGCAAG GGCTGAGTCT GCCACTATAT TCGCAGATAT CGCCACTCCT  780
CATTCAGTTT GGGTCTTCGC ATGTGCTCCA GATCGTTGTC CACCTACAGC ATTATATGTG  840
GCCGGGATGC CGGAGTTGGG TGCATTTTTT GCTATTCTTC AGGATATGAG GAACACCATA  900
ATGGCATCAA AATCTGTGGG GACATCTGAA GAGAAATTGA AGAAAAAATC AGCATTCTAC  960
CAGTCATACT TGAGACGTAC TCAGTCAATG GGGATTCAAC TGGACCAGAA GATAATCATC 1020
TTATACATGA GCCATTGGGG AAGAGAGGCC GTCAATCACT TCCATCTT             1068
```

FIG. 9

SEQ ID NO:19:

GGTTTAGCTC AGGGTTACGT GACAGGTTCA GTGGAAACTA CACCTATTCT CTTAACGCAG 60
GTAGCTGATC TTAAGATTGA GAGTTCTTGT AATTTCGATC TGCATGTCCC GGCTACTACT 120
ACCCAAAAAT ACAATCAGGT TGACTGGACC AAAAAAAGTT CAACTACAGA AAGCACAAAT 180
GCAGGTGCAA CTACATTTGA GGCTAAAACA AAAGAGATAA ATTTAAAAGG CACATGTAAT 240
ATTCTTCCAA CTACATTTGA AGCTGCATAT AAATCAAGGA AGACAGTAAT TTGTTATGAT 300
TTAGCCTGTA ATCAAACACA TTGTCTTCCT ACAGTCCATT TGATTGCTCC TGTTCAAACG 360
TGCATGTCTG TGCGGAGCTG TATGATAGGT TTGCTGTCAA ACAGGATTCA AGTCATATAT 420
GAGAAGACAT ACTGTGTTAC AGGTCAATTA ATAGAGGGGC TATGTTTCAT CCCAACACAT 480
ACAATTGCAC TCACACAACC TGGTCATACC TATGATACTA TGACATTGCC AGTGACTTGT 540
TTTTTAGTAG CTAAAAAGTT GGGAACACAA CTTAAGCTGG CTGTTGAGTT AGAGAAACTG 600
ATTACTGGTG TGAGTTGCAC AGAAAACAGC TTTCAAGGTT ACTACATCTG CTTTATCGGA 660
AAACATTCAG AGCCCTTATT TGTGCCAACA ATGGAAGATT ATAGGTCAGC TGAGTTATTT 720
ACCCGTATGG TTTTAAATCC GAGAGGTGAA GATCATGACC CTGATCAAAA TGGACAAGGC 780
TTAATGAGAA TAGCCGGACC TGTTACAGCT AAGGTGCCAT CTACAGAAAC TGGACAAGGC 840
ATGCAAGGAA TTGCATTTGC TGGGGCACCG ATGTATAGCT CTTTCTCAAC TCTCGTGAGG 900
AAGGCTGATC CTGAGTATGT CTTCTCCCCA GGTATAATTG CAGAATCAAA TCATAGTGTC 960
TGTGATAAGA AAACAGTACC CCTTACATGG ACAGGGTTTT TGGCAGTTTC TGGAGAGATA 1020
GAGAAAATAA CAGGCTGTAC AGTCTTCTGT ACATTGGCAG GACCTGGTGC TAGTTGTGAA 1080
GCATACTCAG AAACAGGAAT CTTTAATATA AACTTCATGT GCCAAAGAGT GAATAAAGTT 1140
CAAAAATTCA GAGGCTCAGA ACAGAGAATC AACTTCATGT GCCAAAGAGT TGATCAAGAT 1200
GTTGTAGTCT ATTGTAATGG GCAA 1224

FIG. 10

SEQ ID NO:20:

```
ATGAGCACCC TCAAAGAAGT GCAAGACAAC ATTACTCTCC ACGAACAACA ACTTGTGACT   60
GCCAGGCAGA AGCTCAAAGA TGCAGAAAGA GCGGTGGAAT TGGACCCCGA TGATGTTAAC  120
AAAAGCACAT TACAGAGCAG ACGGGCAGCT GTGTCTGCAT TGGAGACCAA ACTCGGAGAA  180
CTCAAGCGGG AACTGGCTGA TCTTATTGCA GCTCAGAAAT TGGCTTCAAA ACCTGTTGAT  240
CCAACAGGGA TTGAACCTGA TGACCATTTA AAGGAAAAAT CATCACTGAG ATATGGAAAT  300
GTCCTTGATG TAAATTCCAT TGACCTCGAG GAACCAAGTG GGCAAACAGC TGATTGGAAA  360
TCCATCGGAC TCTACATTCT AAGTTTTGCA TTACCGATTA TCCTTAAAGC CTTGTACATG  420
TTATCTACTA GAGGCCGTCA AACAATCAAA GAAAACAAGG GAACAAGAAT TCGATTTAAG  480
GATGATTCAT CTTATGAAGA AGTCAATGGA ATACGTAAAC CAAGACATCT ATATGTTTCT  540
ATGCCAACTG CTCAGTCTAC AATGAAAGCA GATGAGATTA CTCCTGGGAG GTTCCGTACA  600
ATTGCTTGTG GGTTATTCCC GGCCCAAGTC AAAGCAAGGA ATATTATCAG TCCTGTTATG  660
GGTGTGATTG GCTTTAGTTT CTTTGTGAAA GATTGGATGG AAAGAATTGA TGACTTTCTG  720
GCTGCACGTT GTCCATTTCT ACCCGAACAG AAAGACCCTA GGGATGCTGC ATTGGCAACT  780
AACAGAGCCT ATTTTATAAC ACGTCAATTA CAGGTTGATG AGTCAAAGGT TAGTGATATT  840
GAGGATCTAA TTGCTGATGC AAGGGCTGAG TCTGCCACTA TATTCGCAGA TATCGCCACT  900
CCTCATTCAG TTTGGGTCTT CGCATGTGCT CCAGATCGTT GTCCACCTAC AGCATTATAT  960
GTGGCCGGGA TGCCGGAGTT GGGTGCATTT TTTGCTATTC TTCAGGATAT GAGGAACACC 1020
ATAATGGCAT CAAAATCTGT GGGGACATCT GAAGAGAAAT TGAAGAAAAA ATCAGCATTC 1080
TACCAGTCAT ACTTGAGACG TACTCAGTCA ATGGGGATTC AACTGGACCA GAAGATAATC 1140
ATCTTATACA TGAGCCATTG GGGAAGAGAG GCCGTGAATC ACTTCCATCT T          1191
```

FIG. 11A

SEQ ID NO:21: Nucleotide sequence of the FCV DNA insert of p3H22-S-317 encoding the dominant N-protein epitope (first 100 amino acids).

```
ATGAGCACCC TCAAAGAAGT GCAAGACAAC ATTACTCTCC ACGAACAACA ACTTGTGACT  60
GCCAGGCAGA AGCTCAAAGA TGCAGAAAGA GCGGTGGAAT TGGACCCCGA TGATGTTAAC 120
AAAAGCACAT TACAGAGCAG ACGGGCAGCT GTGTCTGCAT TGGAGACCAA ACTCGGAGAA 180
CTCAAGCGGG AACTGGCTGA TCTTATTGCA GCTCAGAAAT TGGCTTCAAA ACCTGTTGAT 240
CCAACAGGGA TTGAACCTGA TGACCATTTA AAGGAAAAAT CATCACTGAG ATATGGAAAT 300
GTCCTTGATG TAAATTCCAT TGACCTCGAG                                  330
```

FIG. 11B

SEQ ID NO:22: Corresponding amino acid sequence:

```
Met Ser Thr Leu Lys Glu Val Gln Asp Asn Ile Thr Leu His Glu
                 5                  10                  15

Gln Gln Leu Val Thr Ala Arg Gln Lys Leu Lys Asp Ala Glu Arg
                20                  25                  30

Ala Val Glu Leu Asp Pro Asp Asp Val Asn Lys Ser Thr Leu Gln
                35                  40                  45

Ser Arg Arg Ala Ala Val Ser Ala Leu Glu Thr Lys Leu Gly Glu
                50                  55                  60

Leu Lys Arg Glu Leu Ala Asp Leu Ile Ala Ala Gln Lys Leu Ala
                65                  70                  75

Ser Lys Pro Val Asp Pro Thr Gly Ile Glu Pro Asp Asp His Leu
                80                  85                  90

Lys Glu Lys Ser Ser Leu Arg Tyr Gly Asn Val Leu Val Val Asn
                95                 100                 105

Ser Ile Asp Leu
                                                       109
```

FIG. 13

SEQ ID NO:23: Sequence of the majority of the FCV (3H226) M segment:
Nucleic Acid Sequence of 3H226MSEG
Residues: 1 to 3351 of 3351

```
TAGTAGTAGA CTCCGCAAGA AGAAGCAAAC ACTGAATAAA GGAGATACAG AATGGTAGGG   60
TGGGTTTGCA TCTTCCTCGT GGTCCTTACT ACTGCAACTG CTGGGCTAAC ACGGAATCTT  120
TATGAGTTGA AGATAGAATG TCCACATACT GTAGGTTTAG GTCAGGGTTA CGTGACAGGT  180
TCAGTGGAAA CTACACCTAT TCTCTTAACG CAGGTAGCTG ATCTTAAGAT TGAGAGTTCT  240
TGTAATTTCG ATCTGCATGT CCCGGCTACT ACTACCCAAA AATACAATCA GGTTGACTGG  300
ACCAAAAAAA GTTCAACTAC AGAAAGCACA AATGCAGGTG CAACTACATT TGAGGCTAAA  360
ACAAAAGAGA TAAATTTAAA AGGCACATGT AATATTCCTC CAACTACATT TGAAGCTGCA  420
TATAAATCAA GGAAGACAGT AATTTGTTAT GATTTAGCCT GTAATCAAAC ACATTGTCTT  480
CCTACAGTCC ATTTGATTGC TCCTGTTCAA ACGTGCATGT CTGTGCGGAG CTGTATGATA  540
GGTTTGCTGT CAAGCAGGAT TCAAGTCATA TATGAGAAGA CATACTGTGT TACAGGTCAA  600
TTAATAGAGG GGCTATGTTT CATCCCAACA CATACAATTG CACTCACACA ACCTGGTCAT  660
ACCTATGATA CTATGACATT GCCAGTGACT TGTTTTTTAG TAGCTAAAAA GTTGGGAACA  720
CAACTTAAGC TGGCTGTTGA GTTAGAGAAA CTGATTACTG GTGTGAGTTG CACAGAAAAC  780
AGCTTTCAAG GTTACTACAT CTGCTTTATC GGAAAACATT CAGAGCCCTT ATTTGTGCCA  840
ACAATGGAAG ATTATAGGTC AGCTGAGTTA TTTACCCGTA TGGTTTTAAA TCCGAGAGGT  900
GAAGATCATG ACCCTGATCA AAATGGACAA GGCTTAATGA GAATAGCCGG ACCTGTTACA  960
GCTAAGGTGC CATCTACAGA AACAACGGAA ACAATGCAAG GAATTGCATT TGCTGGGGCA 1020
CCGATGTATA GCTCTTTCTC AACTCTCGTG AGGAAGGCTG ATCCTGAGTA TGTCTTCTCC 1080
CCAGGTATAA TTGCAGAATC AAATCATAGT GTCTGTGATA AGAAAACAGT ACCCCTTACA 1140
TGGACAGGGT TTTTGGCAGT TTCTGGAGAG ATAGAGAAAA TAACAGGCTG TACAGTCTTC 1200
TGTACATTGG CAGGACCTGG TGCTAGTTGT GAAGCATACT CAGAAACAGG AATCTTTAAT 1260
ATAAGCTCTC CTACTTGTTT GGTGAATAAA GTTCAAAAAT TCAGAGGCTC AGAACAGAGA 1320
ATCAACTTCA TGTGCCAAAG AGTTGATCAA GATGTTGTAG TCTATTGTAA TGGGCAAAAG 1380
AAAGTCATTC TTACCAAAAC TCTGGTCATA GGCCAATGTA TTTATACATT CACTAGTTTA 1440
TTCTCACTAA TCCTAGGAGT TGCCCATTCT CTTGCCGTAG AGCTATGTGT TCCAGGTCTT 1500
CATGGCTGGG CTACAACAGC ATTACTGATT ACTTTTTGCT TTGGCTGGCT CCTTATACCG 1560
ACAGTCACCT TAATTATACT AAAGATCCTG AGGTTGCTCA CTTTCTCATG CTCACATTAT 1620
TCTACAGAAT CAAAATTCAA AGTTATCTTA GAAAGAGTTA AGGTTGAATA CCAAAAAACA 1680
ATGGGCTCTA TGGTGTGTGA TATTTGCCAC CATGAATGCG AAACAGCAAA AGAACTTGAA 1740
ACACATAAGA AAAGCTGTCC AGAAGGTCAA TGCCCGTATT GTATGACAAT AACTGAATCC 1800
ACTGAGATGG CTCTTCAAGC CCATTTTGCA ATCTGTAAGT TAACAAACAG GTTTCAGGAA 1860
AACTTAAAAA AATCATTAAA ACGCCCAGAA GTACGGAAAG GTTGTTACAG GACACTGGGA 1920
GTTTTTAGAT ACAAGAGCAG ATGTTATGTT GGTTTAGTAT GGGGAATTCT TTTAACAACT 1980
GAACTGATCA TATGGGCAGC CAGTGCAGAA ACCCCCTTAA TGGAGTCTGG TTGGTCTGAC 2040
ACAGCGCATG GTGTGGGCAT AATTCCTATG AAGACAGATT TGGAGCTTGA CTTTGCATCG 2100
GCCTCATCAT CTTCTTACAG TTATAGGCGA AAGCTTATAA ACCCTGCTAA TCAAGAAGAA 2160
ACACTCCCTT TTCATTTCCA GTTAGACAAA CAAGTAGTGC ATGCAGAGAT CCAGAACCTA 2220
GGACATTGGA TGGATGGTAC ATTCAACATA AAAACTGCTT TTCACTGTTA TGGGGAGTGT 2280
AAAAAATATG CCTATCCTTG GCAAACAGCC AAGTGCTTCT TTGAAAAGGA TTATCAGTAT 2340
GAAACAAGTG GGGGCTGTAA TCCACCAGAC TGTCCAGGGG TAGGTACAGG TTGTACAGCT 2400
TGTGGGGTGT ATCTCGATAA GTCCCGTTCG GTTGGGAAAG CATACAAGAT AGTATCACTC 2460
AAATACACAC GGAAGGTGTG TATTCAATTA AGGAACAGAA AAACTTGTAA ACATATAGAT 2520
GTAAATGATT GCTTGGTTAC CCCTTCTGTC AAAGTTTGTA TGATCGGTAC TATATCAAAG 2580
CTCCAACCAG GTGATACTTT GTTGTTCTTA GGCCCTTTAG AGCAGGGTGG GATTATCCTT 2640
AAGCAATGGT GTACAACATC ATGTGTGTTT GGAGACCCCG GTGATATTAT GTCAACGACA 2700
AGTGGGATGA GGTGCCCAGA ACATACTGGA TCTTTTAGAA AGATATGTGG GTTTGCTACA 2760
ACACCAACAT GTGAGTATCA AGGCAACACA GTGTCTGGGT TCAAACGCAT GATGGCAACT 2820
CGAGATTCTT TCCAATCATT CAATGTGACA GAACCACATA TCACTAGCAA CCGACTTGAG 2880
TGGATTGATC CAGATAGCAG TATCAAAGAT CATATTAATA TGGTTTTAAA TCGGGATGTT 2940
TCCTTTCAGG ATCTAAGTGA TAACCCATGC AAGGTTGATC TGCATATACA ATCAATTGAT 3000
GGGGCCTGGG GTTCAGGGGT AGGTTTTACG TTGGTATGCA CTGTGGGGCT TACAGAGTGT 3060
GCAAATTTTA TAACTTCAAT TAAAGCATGT GATTCTGCCA TGTGTTATGG AGCCACAGTG 3120
ACAAATCTGC TTAGAGGGTC AAACACAGTT AGAGTTGTTG GTAAAGGTGG GCATTCTGGA 3180
TCTTTGTTTA AATGCTGCAA TGATACTGAC TGTACCGAAG AAGGTTTAGC AGCATCTCCA 3240
CCACATTTAG ATAGGGTTAC AGGTCACAAT CAAATAGATT CTGATAAAGT TTATGATGAC 3300
GTTGCACCGC CCTGTACAAT CAAGTGTTGG TTTAAAAAAT CTGGGGAATG G          3351
```

HANTAVIRUS-ASSOCIATED RESPIRATORY DISTRESS VIRUS ANTIGENS

This application is a continuation-in-part of Ser. No. 08/120,096, filed Sep. 13, 1993, abandoned, and a continuation-in-part of Ser. No. 08/111,519, filed Aug. 25, 1993, abandoned, and a continuation-in-part of Ser. No. 08/141,035, filed Oct. 26, 1993, abandoned.

BACKGROUND OF INVENTION

The research leading to these inventions was supported by the United States Government, and the Government has certain rights in this Patent.

Field of Art

The invention relates to the HARDS virus, the etiologic agent of Hantavirus-Associated Respiratory Distress Syndrome.

An epidemic of unexplained adult respiratory distress syndrome, affecting primarily residents of the Four Corners region formed by the borders of New Mexico, Arizona, Utah, and Colorado, was recognized in May, 1993. The disease is characterized by a prodromal illness of fever, myalgias, and, in some cases, conjunctivitis, lasting 1–5 days, followed by a severe and acute illness characterized by pulmonary edema and shock. According to the federal Centers for Disease Control and Prevention (CDC), through Jul. 27, 1993, death from suffocation and/or shock had occurred in 14 (78%) of the 18 patients diagnosed with the illness since the epidemic was recognized. The syndrome was eventually determined to be caused by a viral infection of a newly-identified hantavirus virus subsequently named the HARDS virus (also referred to as Sin Nombre Virus and Four Corner Virus, or FCV). According to the CDC, the predominant vector for this virus is the deer mouse Peromyscus maniculatus, which ranges throughout the southwest U.S. with the potential for spreading HARDS infection within this area.

The infection involves two clinical stages. In the first stage, or prodrome, nonspecific abnormalities such as fever, muscle aches, and cough occur, making the distinction between HARDS virus infection and influenza, "Strep throat," and other upper respiratory infections difficult. The prodromal infection lasts only briefly, and is followed in 1–5 days by the second stage of HARDS virus infection, characterized by severe pulmonary disease and shock that often proves fatal. By the time pulmonary edema appears, it is often possible to distinguish HARDS infection from infection caused by other microbes, but many authorities consider that stage to be too late for HARDS virus to be effectively treated by antivirals having potential anti-HARDS activity.

Accordingly, the need for a rapid diagnostic test for the presence of the HARDS virus is particularly acute. In addition to assisting clinicians in determining which patients are infected with HARDS virus and in need of hospitalization and treatment, a specific test for HARDS virus would guide public health officials in their efforts to monitor the extent and spread of the disease. A specific test for HARDS virus would also be helpful for rodent surveillance, studies of the prevalence and transmission of HARDS virus infection, and many other research activities. Such a test would make possible the determination of the range of HARDS virus in rodent populations, thus documenting precisely which human populations are at risk for HARDS infection.

Discussion of Related Art

1. Viral Characterization

By early June, it was recognized that the victims of the new syndrome were developing, during their illness, IgM antibodies that reacted with one or both of two members of the Hantavirus genus of Bunyaviruses. Those viruses are known as Puumala virus, a vole virus that causes the human disease nephropathia epidemica (Europe), and Seoul virus, a virus of Norwegian rats first identified in Korea. Scientists at the federal Centers for Disease Control and Prevention (CDC), in Atlanta, Ga., were able to obtain molecular clones and limited sequence information from the new virus. The sequence information supported the notion that the new virus is a hantavirus; and suggested that its closest relatives among the hantaviruses might be Puumala virus, and another rodent virus known as Prospect Hill virus (PHV).

2. Diagnosis of HARDS Virus Infection

The standard method for diagnosis of acute infections caused by other hantaviruses is the detection, via enzyme-linked immunosorbent assay (EIA), of IgM antibodies to the suspected virus. To do this, it is necessary to have the suspected virus growing in tissue culture; such infected cell cultures are the source of viral antigens to which the patient's serum IgM will react. Thus, for example, serum from a patient with suspected infection by Hantaan virus (which occurs in Korea and China) is incubated with lysate of Hantaan virus-infected cells, and the immune complexes are detected by another antibody.

Despite many attempts to grow the HARDS virus in culture by CDC and others, suitable cultures for the production of viral antigens for the assay of immunoreactive serum antibodies have not been achieved, and thus far, infection by HARDS virus has been diagnosed by one of the following routes:

(a) The development, in infected patients, of antibodies to HARDS virus that can be shown to "cross-react" weakly with antigens derived from Puumala virus or Seoul virus. This method is useful for epidemiologic surveillance, but has proved to be insufficiently sensitive to allow diagnosis of HARDS infection before the patient becomes either critically ill and near death, or has recovered from infection. Infection by HARDS virus appears to result in a somewhat less brisk antibody response than that seen in association with infection by other hantaviruses.

(b) Polymerase chain reaction (PCR). CDC scientists developed a PCR method for diagnosing HARDS infection in June, 1993. A small portion of the G2 gene of the viral M segment is copied into DNA using the enzyme reverse transcriptase, and amplified into large amounts of DNA. The amplified DNA (185 bp) is detected on an agarose gel. Application of this technique to patients presenting to the UNM Hospital in Albuquerque, N. Mex. have shown that the HARDS virus can be detected in the peripheral blood cells of ~90% of infected patients, with no known false-positive tests thus far. The method is somewhat slow (36 hours between receipt of blood and detection of the virus) and appears to be subject to false-negative tests, probably attributable to a sufficient difference in viruses between affected patients to prevent the annealing of PCR primers.

An additional concern in use of PCR is false-positive tests. This problem arises when tiny amounts of amplified viral DNA, present in the laboratory on surfaces, centrifuges, gel apparatuses, etc., finds its way into test tubes used in the preparation of a PCR reaction. The contaminating DNA makes an excellent template for the next PCR reaction, making false-positive tests in uninfected patients a significant risk. The risk can be reduced substantially by strict and rigorous physical separation of facilities used for "pre-PCR" activities (for example, areas where RNA is prepared from the blood of patients to be tested for HARDS virus), and "post-PCR" activities, where amplified viral DNA is studied and analyzed. However, such separation may not be sufficient. In many cases, it is helpful to irradiate PCR cocktails -prior to amplification- with ultraviolet light to destroy contaminating template DNAs, before the bona fide target (patient RNA) is added. However, UV irradiation is much more effective in situations where the contaminating DNA is expected to be at least 300 bases long; for this reason, any contamination by the 185 base-pair product produced by the CDC protocol is unlikely to be "sterilized" sufficiently by UV irradiation. This requirement for larger PCR target is shared by many of the most successful schemes for PCR decontamination (*Nature* 343:27, 1990).

The expense, slow turnaround time, and labor-intensiveness of PCR (as presently configured) makes it a suboptimal solution for rapid diagnosis of hantavirus infection. Nevertheless, PCR may be the best solution available before a definitive serologic (antibody or antigen) test becomes available.

(c) Immunohistochemistry. It is possible to detect HARDS virus antigens in tissue samples of infected patients by exposing the tissues (lungs or kidneys) to a specific monoclonal antibody, originally raised against Puumala virus. This method has been used by CDC in patient tissues obtained at autopsy, but has not been shown to be an effective means of diagnosis in fresh blood samples from living patients.

It is accordingly desirable to provide a rapid method for detecting RNA from the HARDS virus or antibodies to the HARDS virus, especially for clinical serological tests. A reliable source of plentiful amounts of highly antigenic viral antigens suitable for immunoassay applications is particularly desirable.

BRIEF DESCRIPTION OF THE DRAWING

FIG. 5 shows an alignment of the protein encoded by the HARDS virus clone p3H226 S 1129 CR-7 ("NMHV") with those of its closest known hantavirus relatives, Prospect Hill Virus ("PHILL"; GenBank X55128) and Puumala virus strain P360 ("PUUMALA"; GenBank X61035). Regions of identity are indicated with asterisks. Note that many regions of great similarity are present, for example, the highly homologous domain between NMHV coordinates 37 and 193. These regions are the most likely locus for epitopes that are broadly cross-reactive; other regions, such as those between amino acids 194 and 264, are more diverged and will prove to subtend type-specific epitopes within N;

FIG. 6 shows an alignment of the protein (partial sequence) encoded by the HARDS virus clone p3H226 G1 1275 CR-1 ("HARDS") with those of its closest known hantavirus relatives, Prospect Hill Virus ("PHILL", GenBank X55129) and Puumala virus strain P360 ("PUUMALA", L08755). In this domain of G1, no broadly-reactive epitopes have been encountered; instead at least one potent epitope that appears to be specific to HARDS infection has been found. Note several regions of significant divergence between HARDS virus and its relatives, such as coordinates 36 through 93;

FIG. 7 shows the complete nucleotide sequence of the p3H226 S 1129 CR-7 clone subtended by primers used in its amplification.

FIG. 9 shows the complete nucleotide sequence of the FCV-specific portion (lacking primer sequences used in amplification) of p3H226 G1 1275 CR-1. Sequence of the DNA encoding the dominant epitope (the amino acid sequence SCNFDLHVPATTTQKYNQVDWTKKSS (SEQ. ID NO:10) is bolded;

FIG. 10 shows the complete nucleotide sequence of the FCV DNA insert of p3H226 S 1229 pATH-7, which was constructed by ligation of FCV sequences amplified from p3H226 S 419 CR-1 and p3H226 S 1129 CR-7. The artificially-modified sequence that specifies an Xho I site (but does not modify the protein encoded by the N gene) is bolded;

FIG. 11 shows a nucleotide sequence of the clone p3H226 S 317 (A) corresponding to amino acids 1–100 (B) of the dominant N protein epitope;

FIG. 13 illustrates a sequencing of the majority of the FCV (3H226) M segment.

SUMMARY OF THE INVENTION

The invention provides molecularly cloned viral DNA inserts encoding for one or more highly antigenic protein domains of the HARDS virus. The expression of these inserts in suitable expression vectors permits the production of large amounts of viral proteins or oligopeptides from the N, G1, and G2 capsid antigens of the HARDS virus, and identification and isolation of immunodominant and type-specific viral epitopes. The proteins/oligopeptides of the invention may also be synthesized by conventional methods.

The resulting antigens are especially useful in immunoassays for the presence of HARDS antibodies (for example, in patient blood samples), and for the production of antibodies to the HARDS virus in immunosystems for the diagnosis, treatment and prophylaxis of HARDS virus infection.

DETAILED DESCRIPTION OF THE INVENTION

Figure 1:
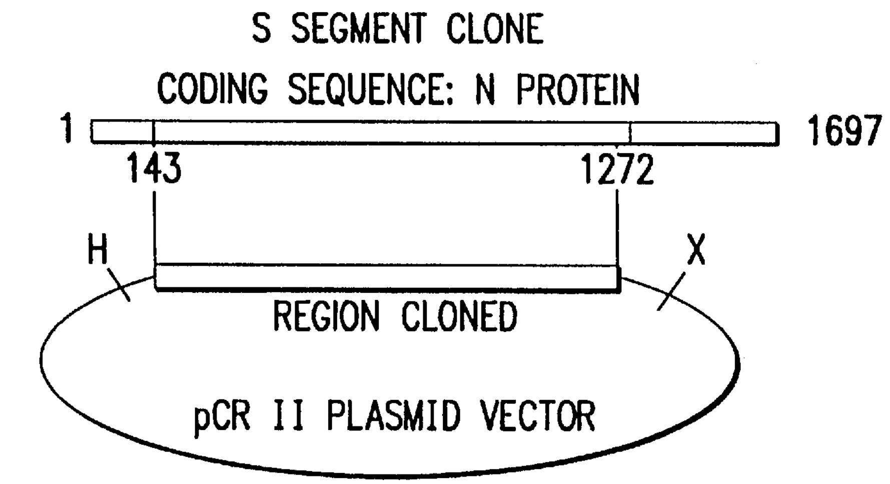
FIG. 1 illustrates the 1129 nt clone obtained from the S segment of the HARDS virus from patient 3H226. PHV S segment coordinates of the clone are 141-1272. H, Hind III site; X, Xba I site.
Figure 2:
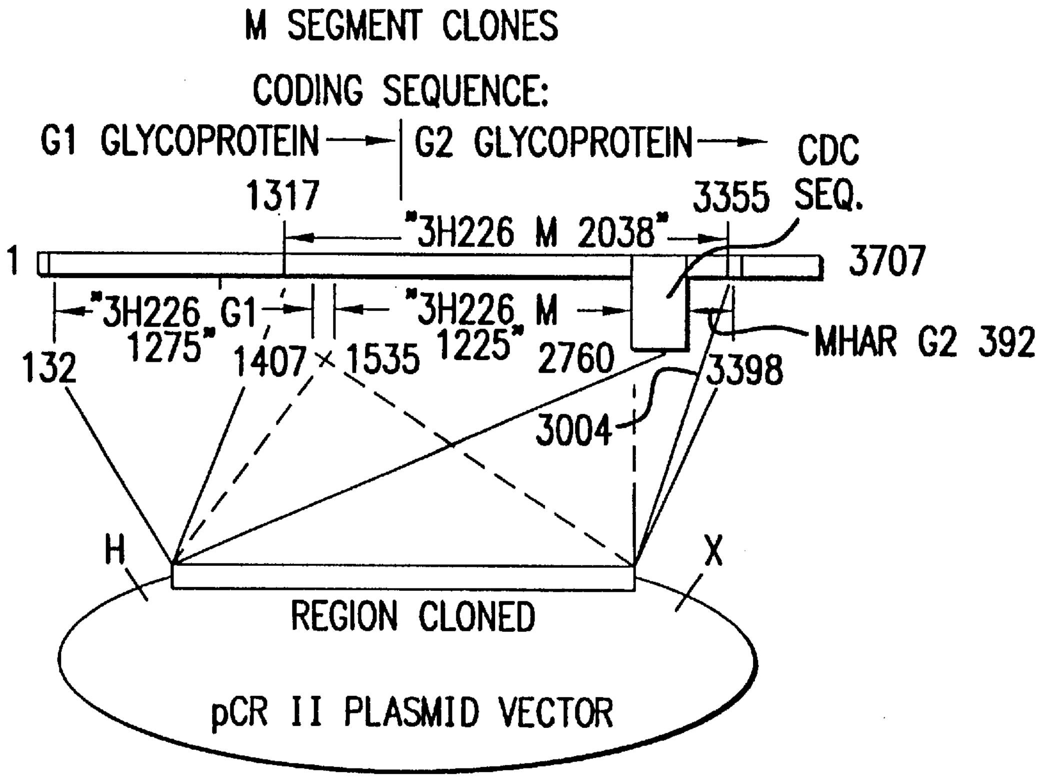
FIG. 2 illustrates M segment clones obtained from the HARDS virus. Four clones containing a total of 3264 nt in four overlapping pieces of viral sequence were obtained. The location of the 241 nt of sequence provided by the CDC is also shown.
Figure 3:
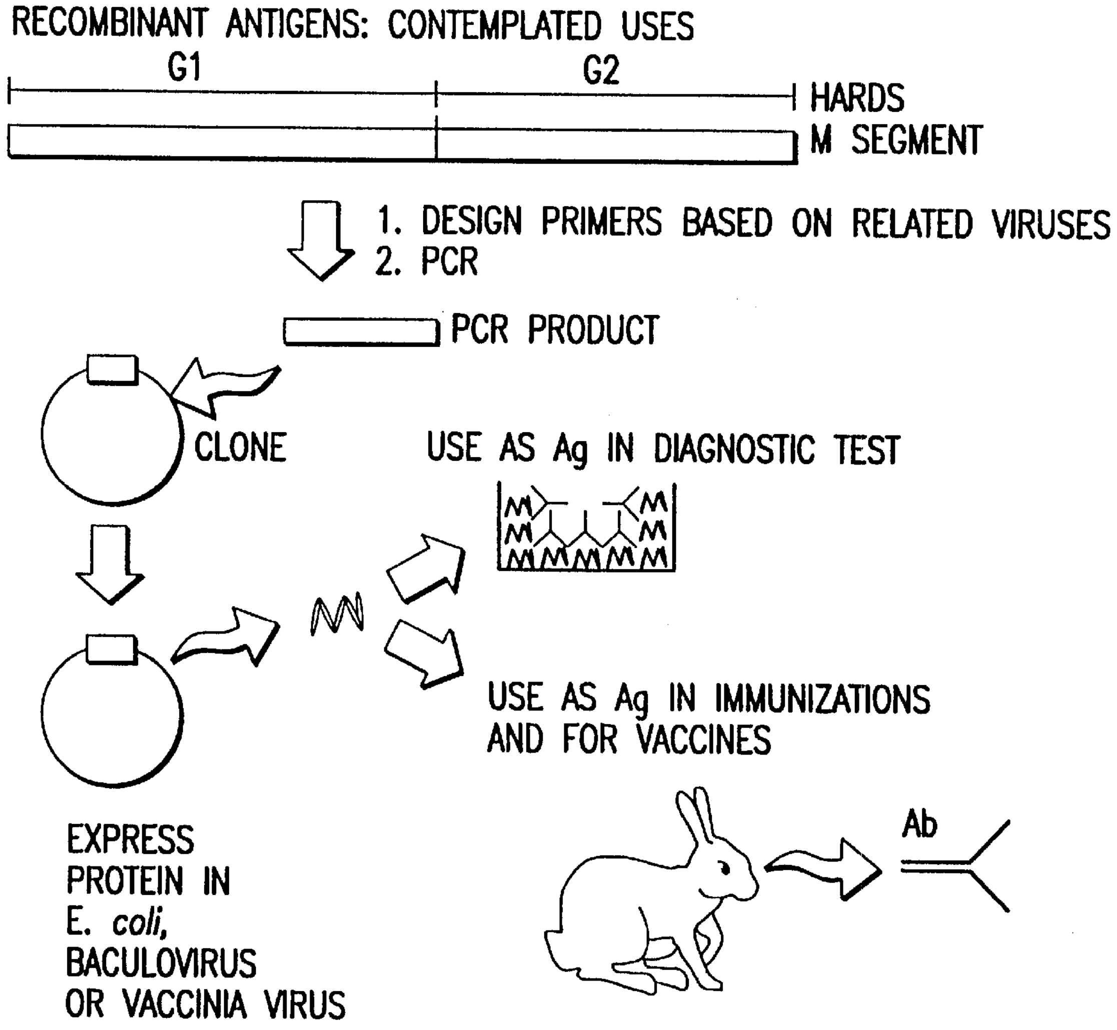
FIG. 3 illustrates uses of the recombinant DNA (rDNA) of the invention.

Of the 3 segments of the hantavirus genome, the M segment (encoding the envelope glycoproteins G1 and G2) and S segment (encoding the nucleocapsid protein, N), appear to encode all or nearly all of the important antigens of the hantavirus capsid. In the present effort, the great majority of the coding sequence of the M and S segments of the HARDS virus (FIGS. 1 and 2) was molecularly cloned, using as template viral RNAs of patients infected with HARDS.

Clones were obtained as follows. By scanning the nucleotide sequences of the complementary DNAs of the M and S segments of Puumala and PHV (publicly available, published information available through the GenBank sequence database, at the NCBI [National Center for Biotechnology Information], a service of the National Library of Medicine [National Institutes of Health], Rockville, Md.), numerous short regions of ~20 nt of sequence conserved between the two viruses were identified. On the theory that any new hantavirus of this serotype might also have retained these conserved sequences, DNA oligonucleotides that corresponded to these sequences or their complements were prepared. Various combinations of such oligonucleotides were used as primers in reverse transcription/polymerase chain reactions (see Examples); the HARDS virus template was provided by lung RNAs from patients 3H226 and MHAR who had died with typical clinical features and pathologic findings of HARDS virus infection (New Mexico Office of the Medical Investigator). Primers were designed to produce a PCR product that would easily clone into bacterial expression vectors, i.e., plasmids designed to allow the ready production of the protein encoded by the foreign DNA insert.

Polymerase chain reactions of the type employed herein to amplify selected DNA oligonucleotide sequences (or their complements) are well-known in the art, and any suitable method may be employed. Alternatively, unamplified sequences may be used, as well as any other method which provides or selected DNA sequence for reaction against a HARDS viral RNA template to provide the insert of the invention.

Primer pairs for use in the PCR/reverse transcription systems are selected for good amplification of the DNA regions of interest, and for the production of easily cloned PCR products. Various methods of cloning PCR products are known in the art, and any suitable method may be used. A particularly useful method known as "TA cloning" (for the introduction of a single T:A base pair between a vector restriction site and a PCR product) is described in Nucl. Acids Res. 19: 1154, 1156 (1991); other useful PCR cloning methods are also described and referenced therein. TA cloning can be done "from scratch", or commercially available cloning systems, such as the TA Cloning Kit available from Invitrogen, may be employed.

As known in the art, the PCR products are cloned into expression vectors to direct the production of large amounts of antigenic viral protein. Various expression vectors may be employed, including bacterial expression vectors (plasmids) and vectors for eukaryotic cells, such as baculovirus and expression vectors for yeast and mammalian cells, which tend to improve duplication of post-translational modifications such as glycosylation of the native viral proteins. The invention is not broadly dependent upon the methods employed to produce the molecular clones of the invention, nor upon the expression vectors or host cells employed, and those recited are exemplary. Protein expression can be optimized by trial and error application of a variety of promoters and host cell strains until high-level expression of the protein encoded by the hantavirus inserts is obtained. Exemplary promoters include the trp E promoter in conjunction with a pATH series of vectors to produce high-expression vectors with multiple cloning sites for construction of trp E fusion proteins (*Methods Enzymol.* 194: 477–90, 1991); or DHFR (Qiagen, Inc., Chatsworth, Calif.); mal E (New England Biolabs Inc., Beverly, Mass.); or bacteriophage T7 (Dr. W. Studler, Cold Spring Harbor Laboratory, Cold Spring Harbor, N.Y.).

After subcloning the cloned PCR product (PCR product ligated to expression vector) into the corresponding host cell, the cells are screened in conventional manner to select clones directing high expression of protein of high antigenicity and specificity, or other characteristics relevant to the intended application. Screening for immunocharacteristics is readily done in conventional manner by assaying the recombinant antigen against HARDS virus antibodies in immunoassay procedures such as enzyme-linked immunoassays, radioimmunoassays or immunoblot (see, e.g., *Science* 244: 359–362, 1989 and *Ann. Int. Med.* 115: 644-649, 1991).

In one embodiment of the invention, after trying multiple primer pairs, ten primer pairs were identified that successfully amplified (and allowed the cloning of) the five large regions that were judged to encode one or more dominant epitopes (highly antigenic protein domains) of the HARDS virus. These regions include a portion of the S segment (FIG. 1) that encodes nearly all of the nucleocapsid protein "N" (the cDNA/mRNA coordinates 141 through 1272 of PHV; the precise coordinates of the HARDS virus itself are not yet known but probably will be similar to those of PHV); and M segment domains (FIG. 2) bounded by coordinates 132 through 1407 of PHV (clone "3H226 G1 1275 "); 1535 through 2760 of PHV ("3H226 M 1225"); 1317 through 3355 ("3H226 M 2038") and 3004 through 3396 of PHV ("MHAR G2 392"). The 241 nt of HARDS virus sequence lying between coordinates 2762 and 3003 (FIG. 2) was provided to the inventor by the CDC.

All of the five regions ("inserts") described above were cloned into the cloning vector pCRII (Invitrogen Corp.) by TA cloning. All inserts were subcloned into bacterial expression vectors pATH10, pATH21, pATH23 and/or pQE60, for the purpose of "expressing" (making in large quantities) the proteins encoded by the DNA inserts.

The Examples provide details of the methods employed.

Utility of the Invention

The products of the invention, including HARDS viral rDNA per se, the DNA inserts (HARDS viral cDNA ligated to an expression vector, including viral cDNA PCR products), and host cells containing the DNA inserts, are broadly useful in the production of antigenic proteins or oligopeptides for diagnostic, prophylactic, and therapeutic applications, particularly immunoassays for, and protective vaccines against, the HARDS virus. Antigenic epitopes according to the invention include both type-specific epitopes highly specific to the HARDS virus, and dominant epitopes strongly reactive with the HARDS virus and other hantavirus such as the Prospect Hill virus. The N protein antigens, in combination with G1 protein antigens, should prove to be particularly useful in detecting and characterizing infections with divergent strains of HARDS virus, particularly for antigenic variations within G1-enclosed type-specific antigen occurring between different virus strains.

Antibody/Antigen Affinity Pairs

The large amounts of homologous viral protein available from the molecular clones of the invention, selected for desired properties, lends the invention to clinical immunoassays and immunotherapies employing either the rDNA antigens or antibodies (both monoclonal and polyclonal) raised against the antigens by known techniques. Immunoassays employing tracer-labelled antibody or antigen such as EIA, ELISA, RIA, RIBA, immunofluorescent assays, and western blot assays are exemplary, as are affinity purifications, standard agglutination and immuno-precipitation assays.

Serologic assays employing DNA antigen for detecting the presence of antibodies to the HARDS virus in blood samples of mammals, either clinically or for assessing the spread of disease in vectors are of particular interest. A detailed description of one such serological assay is set forth in Example III. Also of particular interest is the use of DNA antigen for amplification of a specific signal in such a EIA system. Antibodies complementary to rDNA antigen of the invention are sources of passive immunization to the HARDS virus; such prophylactic interventions after viral exposure have previously been employed in connection with exposure to rabies and hepatitis B virus.

Antibodies to rDNA antigen are readily prepared by textbook procedures such as those described in Methods in Immunology, Garvey et al, eds; W. A. Benjamin, Inc., Reading, Mass. 1977, incorporated herein by reference.

Utility of the HARDS virus rDNA described herein in immunoassays is of great importance owing to the present unavailability of native HARDS virus antigens derived from cultured cells. However, even if such tissue cultures are developed, the rDNA antigens of the present invention will often prove superior to native antigens, as the recombinant antigens can be designed for particular tasks such as discrimination between closely related viruses, with reliable and reproducible results.

Use in Development of Vaccines

Molecular clones encoding a majority of the antigenic domains of the HARDS virus are important vaccine reagents. For example, the HARDS antigen(s) can be expressed in cultured cells under the control of a vaccinia or other heterologous virus'replication machinery, and used to prepare live or killed-virus vaccinia antigens in accordance with known principles. Further, HARDS virus DNA can be used as a substrate for "naked DNA vaccines", e.g., immunization by injection of purified HARDS virus DNA intramuscularly into humans or animals. Additionally, purified HARDS virus proteins, expressed in baculovirus, yeast, or *E. coli*, can be used to immunize humans or animals. As known in the art, immunogenicity of the antigens may be boosted, if necessary, by coupling to haptens. The vaccines of the invention may comprise type-specific epitopes, or combinations of type-specific and cross-reactive epitopes.

EXAMPLES

SECTION I

I. Experimental Methods

A. Design of PCR Primers

The following regions were identified as candidates for primer synthesis by alignment between the Prospect Hill Virus M segment ("PHV"; GenBank accession X55129) and the M segment of Puumala strain K27 ("PUUM"; GenBank accession M14627) as regions with a high degree of nucleotide sequence homology:

| | Name or Coordinate | Sequence (5' to 3') | | | | | | | | |
|---|---|---|---|---|---|---|---|---|---|---|
| PHV | 1 | TAG | TAG | TAG | ACT | CCG | CAA | GAA | GA | (SEQ. ID NO:24) |
| PUUM | 1 | TAG | TAG | TAG | ACT | CCG | CAA | GAA | GA | (SEQ. ID NO:25) |
| Primer | "HanM1+" | TAG | TAG | TAG | ACT | CCG | CAA | GAA | GA | (SEQ. ID NO:26) |
| PHV | 132 | AGA | TTG | AAT | GTC | CTC | ATA | CTG | TA | (SEQ. ID NO:27) |
| PUUM | 132 | AAA | TGG | AAT | GTC | CAC | ATA | CTA | TT | (SEQ. ID NO:28) |
| Primer[a] | "HanMG1NT" | A CCA | TGG | AAT | GTC | CTC | ATA | CTG | TA | (SEQ. ID NO:29) |
| PHV | 1363 | TGT | GTA | CTG | TAA | TGG | CAT | GAA | GAA | (SEQ. ID NO:30) |
| PUUM | 1367 | TGT | TTA | CTG | TAA | TGG | GAT | GAA | GAA | (SEQ. ID NO:31) |
| Primer[b] | "HanM1363+" | TGT | (GT)TA | CTG | TAA | TGG | (CG)AT | GAA | GAA | (SEQ. ID NO:32) |
| PHV | 1382 | AAG | AAG | GTA | ATT | CTT | ACT | AAA | ACC | CT (SEQ. ID NO:33) |
| PUUM | 1385 | AAG | AAA | GTC | ATT | CTC | ACC | AAG | ACC | CT (SEQ. ID NO:34) |
| Primer[b,c] | "HanM1406−" | AAG | AA(GA) | GT(AC) | ATT | CTT | ACT | AAA | ACC | CT (SEQ. ID NO:35) |
| PHV | 1535 | ACA | TTC | TGT | TTT | GGC | TGG | (SEQ. ID NO:36) | | |
| PUUM | 1538 | ACA | TTC | TGT | TTT | GGC | TGG | (SEQ. ID NO:37) | | |
| Primer | "G1P53NOI" | ACA | TTC | TGT | TTT | GGC | TGG | (SEQ. ID NO:38) | | |
| PHV | 1693 | ATG | GTC | TGT | GAG | GTT | TGT | CAG | (SEQ. ID NO:39) | |
| PUUM | 1696 | ATG | GTT | TGT | GAA | GTG | TGT | CAG | (SEQ. ID NO:40) | |
| Primer[b,c] | "HanM1716−" | ATG | GT(CT) | TGT | GA(GA) | GTT | TGT | CAG | (SEQ. ID NO:41) | |
| PHV | 2738 | TTT | AGA | AAG | AAA | TGT | GCA | TTT | GC | (SEQ. ID NO:42) |
| PUUM | 2741 | TTT | AGA | AAG | AAA | TGT | GCA | TTT | GC | (SEQ. ID NO:43) |
| Primer[c] | "HanM2739−" | TTT | AGA | AAG | AAA | TGT | GCA | TTT | GC | (SEQ. ID NO:44) |
| PHV | 3004 | TGG | TGC | ATG | GGG | CTC | AGG | (SEQ. ID NO:45) | | |
| PUUM | 3007 | TGG | AGC | ATG | GGG | TTC | AGG | (SEQ. ID NO:46) | | |
| Primer[b] | "HanM3004+" | TGG | (TA)GC | ATG | GGG | (CT)TC | AGG | (SEQ. ID NO:47) | | |
| PHV | 3332 | TGG | TTT | AAA | AAG | TCT | GGG | GAA | TGG | (SEQ. ID NO:48) |
| PUUM | 3335 | TGG | TTT | AAA | AAA | TCA | GGT | GAA | TGG | (SEQ. ID NO:49) |
| Primer[b,c] | "HanM3355−" | TGG | TTT | AAA | AA(AG) | TC(TA) | GGG | GAA | TGG | (SEQ. ID NO:50) |
| PHV | 3377 | AAT | TGG | ATG | GTA | GTG | GCA | GT | (SEQ. ID NO:51) | |
| PUUM | 3380 | AAT | TGG | ATG | GTT | GTT | GCT | GT | (SEQ. ID NO:52) | |
| Primer[c] | "HanM3376−" | AAT | TGG | ATG | GT(AT) | GT(GT) | GCA | GT | (SEQ. ID NO:53) | |

-continued

| | Name or Coordinate | Sequence (5' to 3') | | | | | | | | | |
|---|---|---|---|---|---|---|---|---|---|---|---|
| The following primers were designed aacording to a similar plan, but using the S segment of PHV (GenBank X55128) or Puumala virus (GenBank M32750) as template for primer design. | | | | | | | | | | | |
| PHV | 4 | TAG | TAG | ACT | TCG | TAA | AGA | GCT | ACT | A | (SEQ. ID NO:54) |
| PUUM | 4 | TAG | TAG | ACT | CCT | TGA | AAA | GCT | ACT | A | (SEQ. ID NO:55) |
| Primer[b] | "HanS3+" | TAG | TAG | ACT | TCT | T(AG)A | A(GA)A | GCT | ACT | A | (SEQ. ID NO:56) |
| PHV | 141 | GGT | GGA | CCC | AGA | TGA | CGT | TAA | CAA | (SEQ. ID NO:57) | |
| PUUM | 141 | AGT | GGA | CCC | GGA | TGA | CGT | TAA | CAA | (SEQ. ID NO:58) | |
| Primer[b] | "HanS143+" | GGT | GGA | CCC | (AG)GA | TGA | CGT | TAA | CAA | (SEQ. ID NO:59) | |
| PHV | 1249 | GGT | GAT | GAT | ATG | GAT | CCC | GAG | CTA | (SEQ. ID NO:60) | |
| PUUM | 1249 | GGT | GAT | GAC | ATG | GAT | CCT | GAG | CTA | (SEQ. ID NO:61) | |
| Primer[b,c] | "HanS1272−" | GGT | GAT | GA(TC) | ATG | GAT | CCC | GAG | CTA | (SEQ. ID NO:62) | |
| PHV | 1309 | AAA | GAG | ATA | TCT | AAC | CAA | GAG | CC | (SEQ. ID NO:63) | |
| PUUM | 1309 | AAA | GAG | ATA | TCA | AAC | CAA | GAA | CC | (SEQ. ID NO:64) | |
| Primer[b,c] | "HanS1341−" | AAA | GAG | ATA | TC(TA) | AAC | CAA | GAG | CC | (SEQ. ID NO:65) | |

[a]The 5' end of HanMG1NT was deliberately altered from that predicted for an "ideal" primer so as to insert an Nco I restriction site (CCATGG) to allow subcloning into the PQE60 vector.
[b]"Degenerate" positions (ie, more than one nucleotide residue used in synthesis of the oligonucleotide) are indicated as parentheses [eg, "(CA)" indicates that C was incorporated into some oligonucleotide molecules, and A in others].
[c]The complement of the indicated sequence was the molecule actually synthesized (ie, antisense strand rather than sense strand).

The following primers were designed according to a similar plan, but using the S segment of PHV (GenBank X55128) or Puumala virus (GenBank M32750) as template for primer design.

In addition to the primers described above, which were all designed on the basis of sequence similarity between Prospect Hill and Puumala viruses, we designed two primers from nucleotide sequences obtained from the HARDS virus itself (the 3' portion of the 3H226 G1 1275 clone). These were:

"HarM 1295+": GTT CAA AAA TTC AGA GGC TCA GAA (SEQ. ID NO:66)

"HarM 1317+": CAA CTT CAT GTG CCA AAG AGT (SEQ. ID NO:67)

B. Reaction Mixes and Conditions: Reverse Transcription and "First Round" PCR

The initial reaction mixes (for reverse transcription and subsequent PCR thermal cycling) were as follows. All mixtures contained 10 pmol of each primer (see Example II) (exception: MHAR G 392 reaction, which had 50 pmol of each primer); 1.7 mM 2-mercaptoethanol; 1.5 mM $MgCl_2$; 10 mM Tris-HCl (pH 8.3); 50 mM KCl; 200 $\mu$M each of dATP, dTTP, dGTP, and dCTP; 10 units of AMV reverse transcriptase (Boehringer-Mannheim), and 2.5 units of AmpliTaq™ DNA polymerase (Perkin-Elmer), in a final volume of 100 $\mu$l. After addition of all reagents to a 0.6 ml Eppendorf tube, the tubes were overlaid with 3 drops of mineral oil (Perkin-Elmer), and placed in a thermal cycler. Each tube was warmed to 42° C. for 1h, then subjected to temperature cycling of 94°–37°–72° for 1 minute, 1 minute, and 3 or 4 minutes per cycle for 8 cycles, then 94°–40°–72° (1 minute, 1 minute, and 3 or 4 minutes) for 32–42 more cycles.

| | | Primers: | |
|---|---|---|---|
| Desired Product | RNA (5 $\mu$g) | Sense | Antisense |
| 3H226 S 1129 | 3H226 autopsy lung | HanS3+ | HanS1341− |
| 3H226 G1 1275 | 3H226 autopsy lung | HanM1+ | HanM1716− |
| 3H226 M 1225 | 3H226 autopsy lung | HanM1363+ | HanM2739− |
| MHAR G2 392 | MHAR autopsy lung | HanM3004+ | HanM3376− |
| 3H226 M 2038 | 3H226 autopsy lung | HarM1295+ | HanM3376− |

C. "Second Round" PCR

After the initial amplification described above, all of the samples except for the MHAR G2 392 amplification were subjected to some form of "nesting" PCR reaction, in which the amplified product was further amplified by using primers internal to those used in the first round of amplification. In the case of the 3H226 M 1225 reaction, the antisense primer was the same primer used in the first round, whereas second round amplification of 3H226 S 1129, 3H226 M 2038, and 3H226 G1 1275 were reamplified with an entirely new primer set. Fifty pmol of each "second round" primer was used; reaction ingredients included 3 $\mu$l of the first-round PCR product, and the same ingredients as those in the first round (except no 2-mercaptoethanol or reverse transcriptase was added):

| | Primers: | |
|---|---|---|
| Desired Product | Sense | Antisense |
| 3H226 S 1129 | HanS143+ | HanS1272− |
| 3H226 G1 1275 | HanMG1NT | HanM1406− |
| 3H226 M 1225 | G1P53NOI | HanM2739− |
| 3H226 M 2038 | Har M1317+ | HanM3355− |

The "second round" PCR product was prepared by thermal cycling at 94–40–72 (1 minute, 1 minute, and 3 minutes, respectively) for 8 cycles, followed by 32–38 more cycles at 94–42–72 (1 minute, 1 minute, and 3 or 4 minutes, respectively) . The reaction was then subjected to an elongation step of 70° for 10 minutes. The second round DNA product (or first round, in the case of MHAR G2 392) was then loaded on an 1.2%–1.6% agarose gel, electrophoresed for 1 h at 80V, and the band of the appropriate molecular weight was then excised with a razor blade. The DNA was extracted from the gel with a glass-milk resin (Qiaex resin, Qiagen Inc.) after melting the gel in a sodium iodide solution.

D. Cloning of PCR Product and Cell Transformation

After washing the resin (according to the instructions for Qiaex resin), the PCR product was taken up in 10 $\mu$l of sterile water, and 5–10 $\mu$l was ligated to the pCRII vector according to the manufacturer's instructions (Invitrogen Corp., San Diego, Calif.). One $\mu$l of the 10 $\mu$l ligation mix was used to transform *E. coli* cells according to the manufacturer's instructions (Invitrogen), and the transformed cells plated onto LB media containing 50 $\mu$g/ml ampicillin and 0.005% X-Gal; plates were incubated at 37° overnight. Clear colonies were selected from the plate the following morning and expanded in 4 ml of LB media containing 50 μg/ml ampicillin.

Plasmid DNA was prepared from the cultures according to standard methods, and then digested with various restriction enzymes to verify that the correct insert had been obtained. Clones that appeared to have the correct restriction enzyme digestion pattern were subjected to DNA sequencing (according to the manufacturer of the Sequenase™ sequencing system, US Biochemicals) to verify that DNA with characteristics appropriate for a novel hantavirus had been amplified and cloned. Specifically, a strong homology to (but not identity to) previously-described hantaviruses Prospect Hill, Puumala, and Seoul virus, and conservation of the protein product that would be predicted from the nucleotide sequence was sought.

For use, the transformed cells are screened by conventional procedures as described above for protein production, and the products screened for desired properties.

II. Description of the Clones

The following table describes some of the characteristics of each of five exemplified clones obtained from above.

| PLASMID DESIGNATION | PRIMERS USED TO AMPLIFY DNA SEQUENCE | RESTRICTION MAP | PARTIAL INTERNAL |
|---|---|---|---|
| p3H226-S1129 CR-7 ATCC accession #75522 | 5'GGTGGACCC(AG)GATGAC GTTAACAA; (SEQ. ID NO:68) 5'TAGCTCGGGATCCAT(AG) TCATCACC (SEQ. ID NO:69) | EcoRI: 3.9 kb; ~.7 kb; ~.4 kb; Xba I, Xho I, Spe I, Sst I, Kpn I: 5.1 kb each | 5'AAGATGGAAG TGATTCACGGC CTCTCTTCCCCA ATGGCTCATGTAT (from 3' end of sense strand) (SEQ. ID NO:1) |
| p3H226-M2038 CR-1 ATCC accession #75532 | 5'CAACTTCATGTGCCAAAG AGT; (SEQ. ID NO:70) 5'CCATTCCCC(AT)GA(CT) TTTTTAAACCA (SEQ. ID NO:71) | Eco RI: 3.9 kb; 1.6, and 0.6 kb; HincII: 5.2 kb and 0.75 kb; Kpn I: 5.9 kb; Xho I: 4.3 kb, 1.0 kb and 0.6 kb; Pst I: 4.8 kb and 1.1 kb. | TACCAAAACTCTGGTC ATAGGCCATGTATT (from 5' end of sense strand) (SEQ. ID NO:2) |
| p3H226-M1225 CR-1 ATCC accession #75525 | 5'ACATTCTGTTTTGGCTGG; (SEQ. ID NO:72) 5'GCAAATGCACATTTCTTTCT-AAA (SEQ. ID NO:73) | Eco RI: 3.9 kb; ~0.8 kb; ~0.4 kb, Bam HI, Kpn I, Xho I: 5.1 kb each, Sal I: uncut; Pst I: ~4.1 and ~1.1 kb, HincII: 4.4 and ~0.8 kb. | 5'GTCCTTAAGCAAT GGTGTACAACATCAT GTGTGTTTGGAGACCC CGGTGATATTGTGTCA ACGACAAGTYG (from 3' end of sense strand) (SEQ. ID NO:3). |
| pH3226-G1-1275 CR-1 ATCC accession #75524 | 5'ACCATGGAATGTCCTCAT ACTGTA; (SEQ. ID NO:74) 5'AGGGTTTTAGTAAGAAT (TG)AC(CT)TTCTT (SEQ. ID NO:75) | Eco RI: 3.9 kb, 1.3 kb Xbs I, Bam HI, Xho I, Sst I, Kpn I: all 5.2 kb. | 5'GGTTTAGGTCAGGG TTACGTGACAGGTTCA GTGGAAACTACACCTA TTCTCTTAACGCAG (from 5' end of sense strand) (SEQ. ID NO:4) |
| pMHAR-G2-392 CR-1 ATCC accession #75523 | 5'TGG(TA)GCATGGGG(CT) TCAGG; (SEQ. ID NO:76) 5'ACTGC(C/A)AC(T/A) ACCATCCAATT (SEQ. ID NO:77) | Xba I, Xho I, Sal I, Sst I, Kpn I: all 4.3 kb. | GTAGGTTTCACATTGG TATGTACTGTAGGGCT AACAGAATGTGCAAAT TTTATAACTTCAAT (from 5' end of sense strand) (SEQ. ID NO:5) |

III. Serologic Immunoassay for HARDS Virus Antibodies

A. Preparation of Antibody

To raise the anti-HARDS antibodies of the invention, rDNA antigen obtained as described above in Example ID is administered to a host animal by customary routes (typically i.p., intraperitoneal) according to well-understood procedures. Host immunoglobulin is then screened for antigen-specific antibody by standard procedures, for example, by affinity chromatography with immunoadsorption of antibody on immobilized, insolubilized antigen. Alternate screening techniques include use of tracer-labelled antigen or tracer-labelled antiglobulin in standard screening immunoassays, typically including precipitation of the product immunogen-antibody complex and quantitation of associated tracer to assess antibody specificity. Of particular importance are enzyme-linked assay procedures, such as standard ELISA protocols employing an immunoreactant-linked enzyme such as peroxidase in systems including a substrate for the enzyme and dyestuff responsive to enzyme activity, radioisotope linked assays such as standard RIA protocols, and Western blot immunoassays.

B. Preparation of Microtiter Plates

The wells of microtiter plates are coated with goat IgG directed against human IgM for immobilization of serum sample antibodies developed against HARDS virus.

C. Enzyme Immunoassay for HARDS Virus Antibodies

Blood samples are applied to the IgG-treated microtiter wells; the wells are then washed, and treated with purified (optionally solubilized) rDNA antigen from Example ID, above. selected for substantial specificity to HARDS virus antibodies.

After washing, the wells are treated with biotin-labelled anti-HARDS recombinant antigen rabbit antibody prepared as in A, above.

A streptavidin-conjugated alkaline phosphatase is used to detect bound biotin-labelled antibody. A chromogenic alkaline phosphatase substrate is used to detect alkaline phosphatase bound to biotin via the streptavidin moiety of the conjugate.

D. Supporting data

Serum samples were tested from four patients (2 patients who were tested within 1–7 days of admission to the hospital, i.e., "acute", and 2 who were tested 22 and 23 days after admission, and were thus "convalescent") . Their serum samples were tested for the presence of specific antibodies in Western immunoblot assays. Antigen targets present on the Western blots were bacterial fusion proteins which contained moieties encoded by the G1 and N clones of the HARDS virus. The bacterial fusion proteins were prepared from lysates of *E. coli* that contained inducible recombinant expression plasmids. The viral fusion proteins included on the Western blot membranes include (a) a protein encoded by the 1275 nt: of HARDS virus G1 sequences of the clone 3H226 G1 1275 CR-1, which had been subcloned into the expression plasmid pATH 23 (Pst I-Kpn I); (b) the entire G1 protein of Puumala virus strain P360; (c) the entire N protein of Puumala virus strain P360; and (d) the protein $p37^{trp\ E}$ with no fused viral domain. After the membranes were incubated with the human serum samples, the membranes were washed and incubated with alkaline phosphatase-conjugated goat anti-human IgG (all four human sera), or goat anti-human IgM (three of the four human sera). In each case, a negative control human serum from a person who had not contracted HARDS was used to probe an replicate western blot membranes in parallel.

Figure 4:
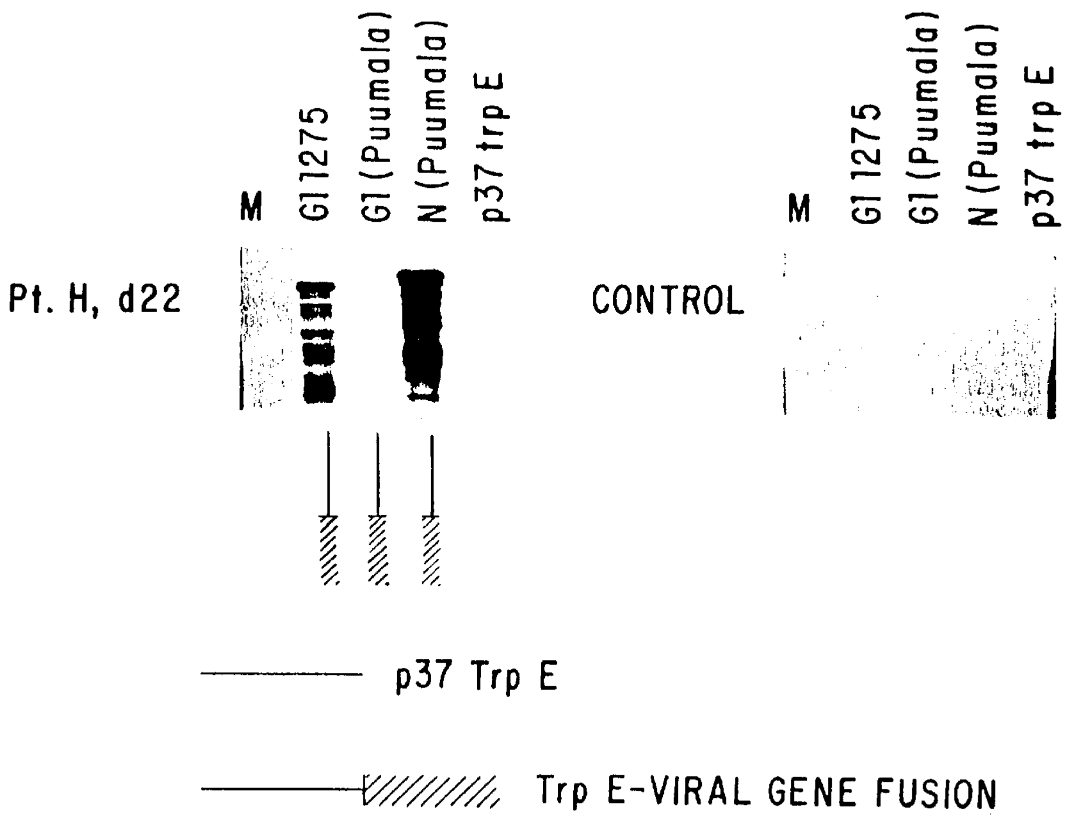
FIG. 4 is serum from patient H (who had recently recovered from a clinically typical case of HARDS) was used to probe a western blot membrane containing a lysate of insoluble protein fraction derived from *E. coli* cultures induced to express trp E protein molecules to which the following viral proteins have been appended as fusion moieties: (a) that protein encoded by the 1275 nt of HARDS virus G1 gene in the clone p3H226 G1 1275 CR-1; (b) the entire G1 gene of Puumala virus strain P360; (c) the entire N protein of Puumala virus strain P360; and (d) the protein $p37^{trP\ E}$ with no fused viral domain. M=molecular weight markers, which bands do not reproduce in this illustration. The blot was probed successively with patient serum, alkaline phosphatase-conjugated goat anti-human IgG, then a color reagent to detect alkaline phosphatase. Patient H's serum reacted briskly to HARDS G1 protein but not at all to the G1 protein of the related Puumala virus. Patient H serum also reacted strongly to Puumala virus N protein. Uninfected human control serum recognized no protein, and neither serum recognized trp E protein by itself.

FIG. 4 shows the typical pattern exhibited by the antibodies of the four individuals. All four individuals' serum samples demonstrated easily detectable and specific anti-hantavirus IgG reactivity, as did all three of those who were tested for anti-hantavirus IgM. Of particular note is the observation that the G1 1275 (HARDS virus) protein reacted strongly with antibodies from all tested patients with HARDS virus infection (IgM and IgG), but the equivalent region of Puumala virus was not recognized at all by any of the four HARDS patients serum antibodies. By contrast, the N protein of Puumala virus reacted strongly with the IgG and IgM of every HARDS patient tested, which strongly supports the hypothesis that the hantavirus N proteins contain epitopes that will be recognized by antibodies directed against all related hantaviruses. The negative control serum did not recognize any virus-specific band, and no serum recognized the trp E protein expressed in the absence of a fused viral protein moiety.

It is contemplated that the insert of the clone p3H226 1129 CR-7, the HARDS virus clone that encodes the large majority of the N protein, expressed as a trp E fusion protein, will contain the epitope(s) present in the Puumala virus N protein, since the Puumala virus N protein was recognized well by HARDS antisera, and that the HARDS virus N protein will prove to have additional or more potent epitopes when probed with anti-HARDS virus serum than Puumala virus N protein, since it is derived from homologous virus.

The nucleotide sequence (and predicted amino acid sequence) of the relevant HARDS virus clones supports the theory that the G1 gene encodes virus-specific epitopes and the N gene encodes more broadly-reactive epitopes. The HARDS virus N protein was strongly conserved (FIG. 5) between HARDS virus and its relatives Puumala and Prospect Hill virus, but large regions of the G1 protein of HARDS virus align poorly with the homologous regions of Puumala and Prospect Hill viruses (FIG. 6). In general, it can be expected that antibodies generated by exposure to divergent proteins will fail to cross-react, but that highly related proteins will tend to elicit antibodies that recognize several members of that protein group (i.e., are cross-reactive).

SECTION II

IV. Experimental Methods

A. Preparation of pATH23-based expression construct designed to allow Trp E-HARDS G1 protein expression (example of methods to be used to generate other expression constructs from other pCRII clones).

The clone p3H226 G1 1275 CR-1 was cut with the restriction enzymes Hind III and Xba I, and the resultant 1.3 kilobase insert was cut out of a 1% agarose gel after electrophoresis. The pATH23 vector [see *Methods Enzymol.* 194:477–90, 1991] was digested with the same enzymes and the digested product (~3.9 kb) was similarly purified from a gel. The 1.3 kb HARDS virus band ("insert") was mixed with the enzyme-digested vector and the Hind III and Xba I-generated ends were joined by T4 DNA ligase via standard techniques. The ligation mix was used to transform competent *E. coli*, strain JM101, and the bacteria were then plated onto plates containing LB media, 1.4% agarose, and 50 $\mu$g/ml ampicillin. Colonies were picked and expanded at 37° while shaking at 300 rpm in LB media containing 50 $\mu$g/ml ampicillin, and plasmid DNA isolated by standard methods. To verify that the cloning was successful, the resultant plasmid clone p3H226 G1 1275 pATH-1 was cut with restriction enzymes that would be predicted to liberate an insert of about 1300 nt and a vector band of 3.9 kb. That is what was observed.

P. Preparation of fusion proteins encoded by Puumala virus.

Molecular clones of the entire M and S segment of Puumala virus strain P360 were provided by Dr. Connie Schmaljohn of the United States Army Research Institute of Infectious Diseases in Frederick, MD (USAMRIID). The molecular clones Dr. Schmaljohn provided were used to generate pATH expression constructs for expression of those proteins of Puumala virus that are homologous to HARDS virus clones generated. These constructs provided a means for ascertaining the degree of cross-reactivity in the immune response of people and animals infected by the HARDS virus and its relatives.

C. Induction of trp E- G1 fusion protein expression.

The methods used to express and purify trp E-hantavirus fusion proteins are provided as an example of methods that one might use to produce large amounts of hantavirus proteins, either fused to another protein or as an unfused, native antigen. Protein expression and partial purification of the fusion protein or unfused $p37^{trp\ E}$ was carried out as described (Methods Enzymol 194:477–90). Briefly, *E. coli* cells (strain JM101) harboring the plasmid p3H226 G1 1275 pATH-1 were expanded in 5 ml of M9 minimal media supplemented with 1 mM $MgSO_4$, 0.1 mM $CaCl_2$, 0.2% glucose, 10 $\mu$g/ml thiamine, 50 $\mu$g/ml ampicillin, 0.5% casamino acids and 30 $\mu$g/ml of L-tryptophan. After reaching stationary phase growth, the culture was added to 45 ml of M9/casamino acids lacking exogenous tryptophan, and grown for 1 hour at 30° with shaking at 300 rpm. At that point indoleacrylic acid was added to a final concentration of 5 $\mu$g/ml, and the induction was carried out for 4–18 hours with continued shaking at 30°. Cells were concentrated by centrifugation and suspended in 10 ml of a buffer containing 50 mM Tris-HCl (pH 8), 5 mM EDTA, and 20 mg lysozyme on ice. The suspended cells were lysed by adding the detergent triton X-100 to a final concentration of 0.8%, and NaCl was added to a final concentration of 300 mM. The insoluble protein fraction was precipitated on ice for 30 minutes, then any remaining unlysed cells were disrupted by sonication. After an additional 30 minutes of precipitation on ice, insoluble protein was pelleted by centrifugation at 16,000×g for 10 minutes. The pellet was resuspended in 0.5 ml of Laemmli buffer containing 0.5% SDS and 5% betamercaptoethanol, and rendered homogenous by sonication. The concentration of hantavirus protein was estimated by separating, via SDS-polyacrylamide gel electrophoresis, the fusion protein from contaminating bacterial products, and estimating the amount of fusion protein by visual inspection of the fusion protein band.

IV. Western Blot Assays

Approximately 5 μg of recombinant $p37^{trp\ E}$-viral fusion protein obtained as above (or $p37^{trp\ E}$ itself) was loaded per lane of a 12.5% polyacrylamide gel for SDS-PAGE. After electrophoretic separation at 200 V for 45', the gel was placed into a western blot electrophoretic transfer apparatus and the proteins electrophoretically transferred onto a nitrocellulose membrane 1 hour at 4° at 100 V, with the gel proteins transferred toward the cathode.

Sera for use as probe in western blot assays were preadsorbed at a concentration of 1:200 against *E. coli* antigens by overnight incubation at 4° in a buffer containing 20 mM TrisHCl pH 7.5 and 0.5M NaCl ("TBS"), 1% powdered milk (Carnation), 5% lysed *E. coli* antigens (see below), 0.1 Triton X-100, and 0.1% deoxycholic acid. *E. coli* antigens were produced by induction of $p37^{trp\ E}$ in 100 ml of JM101cells for 4h as described above; the cells were then pelleted at 3000×g for 10 minutes and the pellet suspended in 3.6 ml of buffer containing 50 mM Tris-HCl pH 8.0, 2% SDS, and 5 mM EDTA. The cells were lysed by sonication until hot, heated in a boiling water bath for 5 minutes, and added to a final concentration of 5% in the above-mentioned preadsorption buffer. The precise contents of the preadsorption buffer, if needed, will need to be adjusted and optimized for each system of protein expression and according to the antibody specificity and immunoglobulin subtype being examined.

The membranes were placed in a tray and were pretreated by immersion in 1% powdered milk in TBS wash buffer for 30 minutes at room temperature. After removing the milk buffer, the serum/preadsorption buffer was then added to the tray and incubated overnight at 4°, with rocking. In the morning, the serum/preadsorption mixture was removed and the membranes washed three times in wash buffer. An alkaline phosphatase-conjugated goat anti-human antibody directed against human IgG or IgM (diluted 1:1000 in 1% milk in TBS with or without detergents) was then used to overlay the membrane and the antihuman Ig antibody allowed to bind for 2 hours at room temperature. The membranes were then washed again three times in wash buffer, and then exposed to a substrate (nitro blue tetrazolium and BCIP) that produces a chromogenic product in the presence of alkaline phosphatase. After sufficient color development (3–20 minutes), the membranes were washed repeatedly in water to remove residual substrate.

VI. Conclusions

1. The G1-encoded protein expressed from one of the cDNA clones of the HARDS virus (p3H226 G1 1275 CR-1) contains an antigenic epitope recognizable by antibodies from patients infected with HARDS virus but not by antibodies from patients infected with closely-related hantaviruses (Puumala virus, for example).

2. The N-encoded protein of HARDS virus (clone p3H226 S 1129 CR-7) contains a broadly-reactive epitope that is recognized by human antibodies produced in response to HARDS virus infection and that also reacts with antibodies produced in response to infections with closely-related hantaviruses (Puumala virus, for example. This antigen appears to be a particularly dominant antigen for early, sensitive and specific detection of infection by the RNA HARDS virus and its relatives. It should prove to be particularly useful in detecting and characterizing infections with divergent strains of HARDS virus, particularly if antigenic variation within the G1-encoded type-specific antigen occurs among different strains.

3. The "HARDS-specific epitope" region of G1 from related hantaviruses each possess a comparable epitope that will also elicit antibodies specific to the virus eliciting the antibodies. That will also extend to new hantaviruses as they are discovered, and thus allow the development of a PCR-based method for amplifying the G1 epitope region from old or new members of the hantavirus genus, allowing extremely rapid development of type-specific diagnostic kits for new pathogens of this class.

4. The description of the G1 and N encoded proteins containing antigenic epitopes of HARDS virus provided herein permits the ready identification and isolation of viral antigens from tissue cultures infected with the virus, according to known techniques. Further, synthetic equivalents of the described proteins are easily made in a text book exercise for use as described herein, if desired.

The described epitopes identified in the G1 and N proteins of the HARDS virus appear to be determined by a very limited sequence of amino acids. It is expected that the dominant epitopes will be contained within less than 20–30 amino acids of HARDS virus sequence. According to the experience of the coinventors and that of others (working on viruses other than hantaviruses), it is expected that other hantaviruses will prove to have a type-specific epitope within the region of G1 that is homologous to that containing the type-specific epitope of the HARDS virus. A PCR system to allow the amplification, using conserved primers flanking the nucleotide sequence encoding the dominant epitope, the immunodominant region of any new hantavirus can thus be developed according to known principles.

SECTION III

IV. Experimental Methods

A. Amplification of HARDS Virus S Segment Nucleotide Sequence

An additional portion of the HARDS virus (HHV) S segment representing nucleotide positions 4 through 423 was cloned, producing a clone p3H226 S 419 CR-1. This clone contains the initiating ATG of the HHV N protein. The nucleotide sequence of that portion of p3H226 S 419 CR-1 that does not overlap the previous S segment clone, p3H226 S 1129 CR-7 was determined. Based upon those sequences, a PCR primer that allows the convenient amplification, subcloning and expression of the first 100 amino acids of the new clone was designed. That (sense) primer has the sequence T ACG ACT AAG CTT ATG ACG ACC CTC AAA GAA G (SEQ. ID NO:78), where the bolded nucleotides make up a recognition site for the enzyme Hind III, and are followed by authentic HHV sequence, beginning with the ATG encoding the initiating methionine of N protein. For amplification and subcloning of the N-terminal 100 amino acids of HHV, an antisense primer was designed with the sequence 5' TGG TTC CTC GAG GTC AAT GGA ATT TAC ATC AAG 3' (SEQ. ID NO: 79). This primer was also based upon authentic HHV sequence, except that the native sequence 5' CTA GAA was replaced with the sequence CTC GAG. The complement of this palindromic sequence is bolded in the above primer sequence. CTC GAG specifies a recognition site for the restriction enzyme Xho I, but does not alter the sequence of the protein encoded by the N gene.

After amplification of p3H226 S 419 CR-1 with the above sense and antisense primers, a 317 bp product was obtained and digested with Hind III and Xho I. A plasmid derivative of pATH 23, called pATH HT-1 was also digested, with the same two enzymes. (pATH HT-1 was originally prepared by digesting pATH 23 with Xba I and Kpn I, and inserting a double-stranded oligonucleotide designed to have the "sticky ends" of Xba I and Kpn I on either side, an Xho I site, and 6 histidine codons internally.) The PCR product, now about 299 nt long after digestion, was inserted into pATH HT-1 with T4 DNA ligase. The resulting expression construct, which produces an abundant soluble protein product of about 52 kD apparent MW (AMW) upon induction, was called "p3H226 S 317 pATH-1". As discussed below, the 100 aa of HHV N protein included in the fusion protein product produced by induction harbors a potent antigenic epitope for humans infected with HARDS virus.

B. Preparation of Expression Constructs for Production of trpE-HHV N-protein Fusion Proteins An expression clone was constructed for expressing the first 407 amino acids of HHV N protein. The plasmid p3H226 S 1129 CR-7 contains coding sequence of the N protein gene that lies downstream of, but overlaps with, that of HHV clone p3H226 S 317 pATH-1. The coding sequences of p3H226 S 317 pATH-1 were joined to those of p3H226 S 1129 CR-7 to produce a larger expression construct that would allow the expression of all of the HHV N gene DNA present in a single protein molecule. To do that, a sense primer for PCR was prepared that overlapped with the antisense primer used to prepare p3H226 S 317 pATH-1. The region of overlap is the artificial Xho I site. The sense primer for amplification was thus ATT GAC CTC GAG GAA CCA AGT GGG CAA ACAG (SEQ. ID NO:80). For the antisense primer, a new version of the primer originally used to generate p3H226 S 1129 CR-7 was selected. The new version of the Han S 1272-primer differed from the old primarily in that it contains a recognition site for the restriction enzyme Xba I near its 5' end: G GCT TCT AGA GGG ATC CAT GTC ATC ACC (SEQ. ID NO:81).

Figure 8:
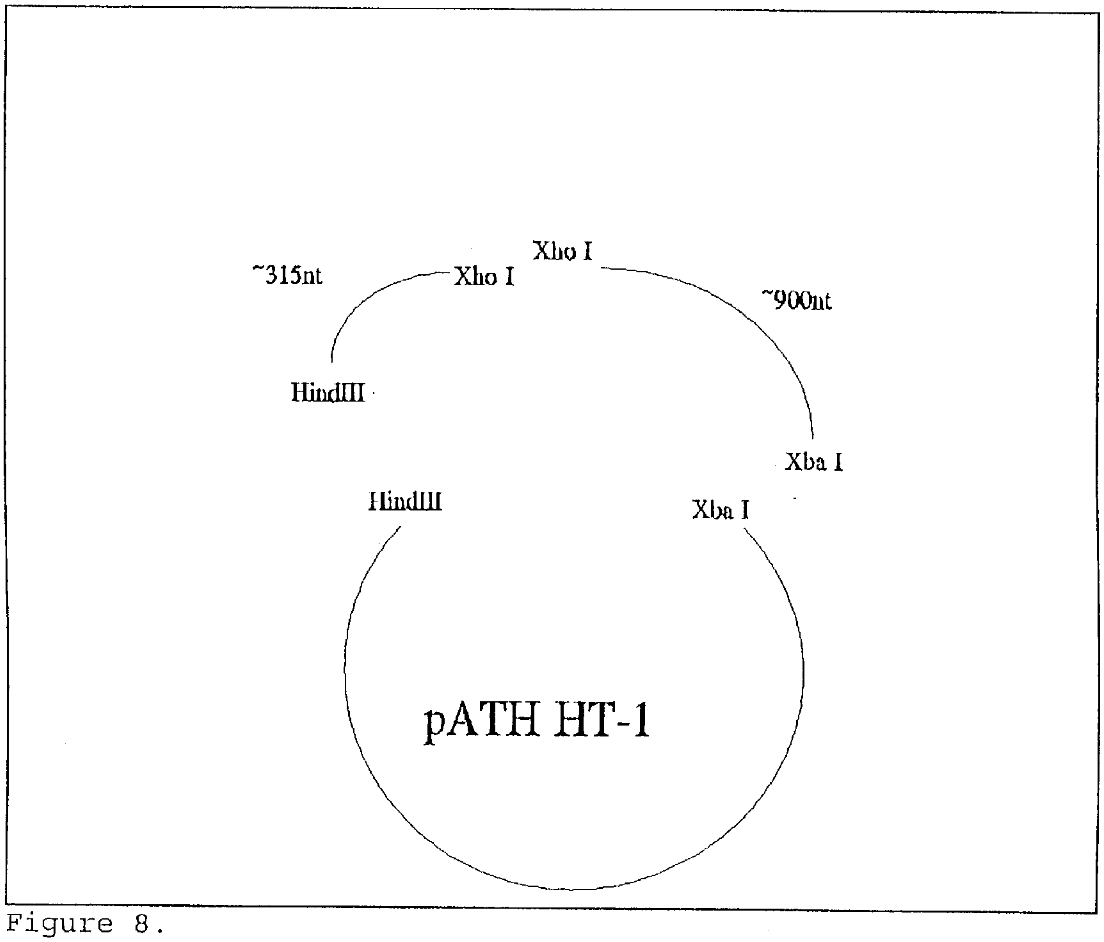
FIG. 8 illustrates the preparation of p3H226 S 1229 pATH-1 by three-way ligation.

Using p3H226 S 1129 CR-7 as template, an amplimer of about 900 bp was prepared by PCR with the above two primers. The amplimer was digested with Xho I and Xba I and was ligated to the ~299 bp Hind III/Xho I- digested amplimer described in (a) above, as well as pATH HT-1 that had been digested with Hind III and Xba I. A "three-way" ligation ensued (FIG. 8).

The resultant product was called p3H226 S 1229 pATH-7 (FIG. 10). It has been shown to have the correct restriction map, including two Xho I sites and one HindIII site spaced an appropriate distance from one another, and it produces a large amount of an insoluble trp E fusion protein of AMW ~75–78 kD after standard induction.

Expression constructs that produce other trp E-HHV N protein fusion proteins have been produced. The insert of p3H226 S 1129 CR-7 was subcloned into pATH 10 and used to produce p3H226 S 1129 pATH-1, as well as to subclone the ~750 bp Eco RI-Eco RI fragment of p3H226 S 1129 CR-7 into pATH 1 to produce p3H226 S RI pATH-1. Both of these expression constructs make large amounts of insoluble trp E-HHV N protein fusions that contain portions of the HHV N protein produced by p3H226 S 1229 pATH-7.

C. Preparation of Expression Constructs for Production of PHV Fusion Proteins

The two portions of the Prospect Hill virus (PHV) genome that correspond to the HHV sequences of clones p3H226 G1 1275 CR-1 and p3H226 S 1129 CR-7 were cloned for use in determining whether the antigenic epitopes identified within the above two HHV clones induce antibodies would cross-react with HHV's nearest relative, PHV. The PHV template was derived from a virus stock obtained as a gift from Richard Yanagihara of National Institutes of Health in July, 1993. Yanagihara's PHV stock was used to infect Vero E6 cells and PHV was propagated in the biosafety 3 facility of University of New Mexico. The PHV cDNAs were cloned from RNA prepared from those infected cultures under conditions identical to those used to clone the corresponding portions of HHV (described above). The resulting clones were called pPHV G1 1275 CR-1 and pPHV S 1129 CR-1. The PHV inserts were moved from the pCR II vector and transferred into pATH expression vectors in a manner substantially identical to that used to produce pATH expression constructs p3H226 G1 1275 pATH-1 and p3H226 S 1129 pATH-1. The expression constructs proved to be good producers of insoluble trp E fusion proteins of the appropriate size.

D. HHV G1 Epitope

The location of the dominant epitope specified by the protein product of the 1275 nt HHV G1 gene clone was determined to within 23 amino acids. The antibody response to that epitope was found to be specific to infection by HHV: serum samples from patients with HARDS do not recognize any determinant in the 1275 nt G1 protein of PHV (HARDS patients lack antibodies cross-reactive with Puumala virus G1 protein, see III D, above).

To map the epitope of HHV G1, ~20 serial exonuclease/S1 nuclease deletions of the plasmid p3H226 G1 1275 pATH-1 were prepared, after linearization with restriction enzymes recognizing sites at the 3' end of the insert (according to the instructions of the Promega Erase-a-Base™ system, Promega Corp.; see *Gene* 28:351–359, 1984). Each new deletion construct was induced to express its corresponding trp E-HHV G1 fusion protein. The series of fusion proteins were characterized according to their apparent MW, and a selection of proteins of various size were transferred to nitrocellulose membranes for western blot analysis. The western blot membranes were probed with serum samples from each of 2 individuals who were convalescing from HHV infection, followed by alkaline phosphatase-conjugated goat anti-human IgG. The smallest protein in the series that continued to exhibit reactivity with HARDS patient serum samples was the product of that clone that contained DNA sequences specifying amino acids 37 through 91 of G1 (using PHV M segment coordinates, beginning at the initiating methionine of PHV). Both patient serum samples were strongly reactive with that truncated protein, but lacked reactivity to the protein produced by the next largest member of the deletion series, which included amino acids 37 through 66. It was concluded from this that the epitope of the protein product of p3H226 G1 1275 pATH-1 that is recognized by patients with HHV infection lies between amino acids 66 and 91 of the G1 protein. The sequence of amino acids in that portion of the protein is SCNFDLHVPATTTQKYNQVDWTKKSS (SEQ. ID NO:10). Negative control serum samples from people presumed to have had no exposure to HHV lacked reactivity to the protein product of any member of the deletion series.

Protein products of the PHV clones pPHV G1 1275 pATH-1 and pPHV S 1129 pATH-1 were tested for reactivity against the serum samples of two patients convalescing from HHV infection. Moderate reactivity to the N protein product of pPHV S 1129 pATH-1 was observed (although less brisk than that observed with the product of the HHV N gene clone p3H226 S 1129 pATH-1, ATCC #75561), but no reactivity to the product of pPHV G1 1275 pATH-1 (C, above). These results confirm the previous observation that humans infected with HHV produce antibodies to the HHV G1 protein that do not cross-react with other hantaviruses (Puumala virus and PHV). Thus, the HHV G1 protein epitope described is HHV antibody-specific and highly useful for differentiation of antibodies responsive to HHV infection from antibodies responsive to PHV infection, Puumala virus infection, or infection by other hantaviruses yet to be identified.

E. HHV N-protein Epitopes—Expression Constructs and Antigen Activity

At least two independent epitopes of HHV N protein, which can be used independently in serologic assays for HHV infection in man have been identified. Four plasmid constructs designed to express different domains of HHV N protein were produced as described above. An additional clone, not described above, spans only the 3' 262 nt of the insert and 3' PCR primer of p3H226 S 1129 CR-7, and is called p3H226 S 238 pATH-1. The following Table describes characteristics of five clones:

| Clone name | Fusion Protein (AMW) | PHV Coordinates (nt/aa) |
|---|---|---|
| p3H226 S 1229 pATH-7 | ~78 kD | 43-1272/1-407 |
| p3H226 S 317 pATH-1 | ~52 kD | 43-343/1-100 |
| p3H226 S 238 pATH-1 | ~45 kD | 1008-1272/322-407 |
| p3H226 S RI pATH-1 | ~60 kD | 509-1272/155-407 |
| p3H226 S 1129 pATH-1 | ~75 kD | 141-1272/34-407 |

Fusion proteins were produced in large amounts from each of these constructs, and used in western blot format to detect serum IgG antibodies from patients with HARDS. For each of 8 serum samples from patients with acute (5) or convalescent (3) HHV infection, intense and specific seroreactivity was demonstrated against the 52 kD product of p3H226 S 317 pATH-1 and the 78 kD product of p3H226 S 1229 pATH-7, but not against the 45 kD product of p3H226 S 238 pATH-1. All HHV/HARDS sera tested were also active against the intact Puumala N protein, but at diminished intensity compared to the proteins encoded by authentic HHV N gene clones. A negative control serum from a normal blood donor did not recognize any of the recombinant fusion proteins, and no serum reacted with $p37^{trp\ E}$ lacking an HHV fusion moiety. These studies showed that the first 407 amino acids of HHV N protein contain at least one potent epitope, and that at least one of those epitope(s) is present in the first 100 amino acids. No epitopes were judged to be present in amino acids 322–407.

A second experiment examined the reactivity of proteins expressed by all of the above constructs (except for p3H226 S 238 pATH-1, which did not appear to encode any significant epitopes), using as probe convalescent serum samples from two patients with HHV-HARDS. The intense and specific reactivity to amino acids 1–407 was again observed, as was intense reactivity to amino acids 1–100. Significantly, moderate IgG seroreactivity with both was also observed in the products of p3H226 S RI pATH-1 and p3H226 S 1129 pATH-1. The reactivity of the product of p3H226 S RI pATH-1 was significant because that construct has no sequences overlapping with those of p3H226 S 317 pATH-1, where a dominant antigenic determinant had already been localized. A negative control serum again failed to recognize any fusion protein, and no serum recognized $p37^{trp\ E}$ lacking an HHV fusion moiety. These experiments demonstrate that infected patients react to at least 2 specific epitopes of HHV N protein. One such epitope is localized within the first 100 amino acids, and the other is subtended by amino acids 155 through 407. Based upon the lack of antigenic activity of the protein coordinates 322–407, it appears that the epitope(s) between 155–407 lies between amino acids 155 and 321. The identification of the second epitope of N (between aa 155 and 321) allows for the development of a "3-antigen" recombinant diagnostic system that should be an improvement over our previously-described 2-antigen western blot.

F. Detection of HARDS Virus Antibodies

The 2-antigen recombinant western blot assay developed (and described previously) is used for detecting serum IgG or IgM antibodies from patients infected with HHV, even in the earliest stage of infection, and reliably diagnose acute HHV infection. In a blinded study of 30 serum samples, of which 20 were derived from control patients who were presumably never exposed to HHV, and of which 10 came from 8 patients with HHV infection, manifested as HARDS. Using alkaline phosphatase-conjugated goat anti-human IgG or -IgM as secondary antibody, bound antibodies were detected from all 10 samples from patients with HARDS (reactive with both HHV G1 and Puumala virus N protein). All 10 patients had reactivity to both antigens with IgG; 9 of the 10 had reactivity to both antigens with IgM. Of the controls, one demonstrated IgG reactivity to Puumala N protein in isolation; s/he was labeled "indeterminate" and correctly identified as uninfected. Although the blinded study was conducted with N protein derived from Puumala virus, subsequent data prove convincingly that HHV N protein reacts even more intensely with serum samples from patients with HHV infection than does Puumala N protein, and will prove to be a more sensitive indicator of HHV infection.

SECTION IV

Serum samples from 31 patients in the acute stage of HARDS (all within 2–3d of admission to the hospital, or, in the case of 7 patients, their death and subsequent autopsy) were tested. All samples had IgM and IgG reactivity by Western blot with that portion of the HARDS virus N protein encoded by clones p3H226 S 1229 pATH-7 and p3H226 S 317 pATH-1. 31 of the 31 and 26 of the 31 had IgG or IgM reactivity, respectively, with the protein encoded by the G1 protein expression construct p3H226 G1 1275 pATH-1. The dominant epitope of the FCV N protein appears to be contained within the first 110 amino acids.

A. Determination that one or more epitopes encoded by the clone p3H226 S 317 pATH-1 are cross-reactive with a homologous portion (ie, the first 110 amino acids) of the Prospect Hill virus (PHV) N protein.

That portion of the PHV N protein gene was cloned by reverse transcriptase PCR as above, using RNA prepared from PHV-infected Vero cell cultures. The sense primer for PHV was synthesized specifically for amplification of PHV cDNA and had the sequence T ACT ACA GTC GAC GGG ATG AGC CAA CTC AGG GA (SEQ. ID NO:82). The antisense primer was the same as that used above to amplify the corresponding portion of FCV cDNA and had the sequence TGG TTC CTC GAG GTC AAT GGA ATT TAC ATC AAG (SEQ. ID NO:83). The amplified DNA was gel-purified and digested with the restriction enzymes Sal I and Xho I (recognition sites for which are present in the above primers) and cloned directly into Sal I- and Xho I-digested pATH HT-1. The resulting construct was called pPHV S 317 pATH-1.

Trp E fusion protein was expressed from pPHV S 317 pATH-1 obtained from PHV according to standard protocol.

Soluble protein was compared to that expressed from p3H226 S 317 pATH-1 according to the invention, and subjected to Western blot analysis using 8 serum samples from patients with HARDS as the source of antibodies. Both the FCV and PHV proteins were reactive with all 8 HARDS serum samples.

Conclusion: A dominant epitope contained within the first 110 amino acids of FCV is cross-reactive with its PHV homolog.

B. Location of the dominant epitope of N protein encoded by the plasmid clone p3H226 S 317 pATH-1.

Figure 12A:
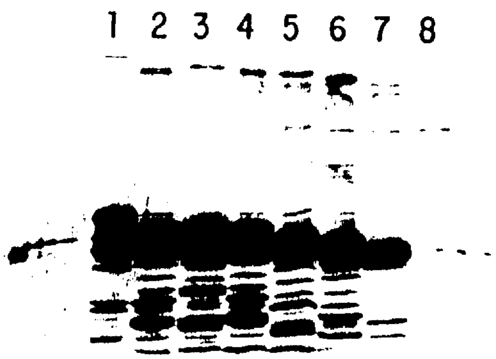
FIG. 12 shows a Western immunoblot showing reactivity of a carboxy-to-amino terminal nested deletion series derived from p3H226 S 317 pATH-1 with two HARDS patient sera (panels A and B) or a control serum (panel C). Expressed proteins include that from p3H226 S 317 pATH-1 itself (lane 1), as well as a series of 6 proteins of decreasing size that continued to react with the HARDS patient serum antibodies (lanes 2–8). The carboxy-terminus of the dominant epitope of FCV N protein is encoded by the DNA sequence that is present in clone 7 but lacking in clone 8.
Figure 12B:
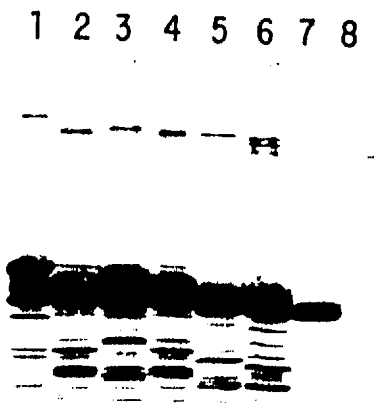
Figure 12C:
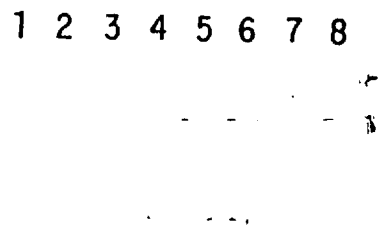

Mapping was accomplished by producing a nested set of 3' and 5' deletions of the DNA insert of this clone and expressing the truncated insert as protein (*Gene* 28:351–359). FIG. 12 shows a Western blot produced by reacting trp E fusion proteins expressed from various members of a nested deletion series with serum (1:200 dilution) from two patient with HARDS (panels A and B) or an uninfected control (panel C). This deletion series was produced by linearizing the p3H226 S 317 pATH-1 plasmid in the polylinker sequence lying 3' of the FCV nucleocapsid gene insert and digesting the 3' end of the viral cDNA to varying extents with exonuclease III. A series of proteins were produced that had sustained larger and larger C-terminal deletions, and were thus smaller and smaller in size. Several members of the deletion series were reactive with serum samples from all 5 HARDS patients tested. The smallest protein that continued to be reactive with the 5 HARDS serum samples contained amino acids 1 through 59 of the FCV N protein. By contrast, the next smallest member of the N protein deletion series failed to react with any HARDS patient serum sample. The nucleotide sequence of that clone showed that it encoded amino acids 1 through 41 of FCV N protein. These studies showed that the carboxy terminus of the dominant epitope of FCV N protein lies between amino acids 41 and 59.

The amino terminus of the epitope was mapped by preparing an amino-terminal deletion series from p3H226 S 317 pATH-1. This series was constructed by synthesizing selected sense primers designed to allow PCR amplification of DNAs from a p3H226 S 317 pATH-1 template, using the same antisense primer that was originally used to make p3H226 S 317 pATH-1. The sense primers were designed so that pATH HT-1 subclones prepared from the amplified DNA would encode in-frame trp E fusion proteins lacking varying amounts of the amino-terminus of the N protein.

For two of the five HPS serum samples tested, FCV N IgG antibodies reacted with the amino-to-carboxy terminus deletion construct p3H226-S-NEx91 (aa17–aa110) and did not react with p3H226-S-CEx136 (aa32–aa110). These reactivities placed the amino terminus boundary of the epitope between aa17 and aa32. For these two serum samples, the epitope mapping data indicate that an epitope is present between FCV N aa17 and aa59. The amino acid sequence of this segment is QLVTARQKLKDAERAVELDPDDVNKSTLQSRRAAVSALETKLG (SEQ. ID NO:6). The sequences of the corresponding portion of PHV and Puumala virus N proteins is QLVIARQKLKEAERTVEVDPDDVNKSTLQSRRSAVSTLEDKLA (SEQ. ID NO:7) and QLVVARQKLKDAERAVEVYPDDVNKNTLQARQQTVSALEDKLA (SEQ. ID NO:8). For the other three HPS serum samples tested, antibody reactivity was observed to all of the amino-to-carboxy terminal deletion clones that were tested (extending to aa60). These reactivities indicate that the N segment in p3H226 -S-330 contains a second antibody-reactive epitope that is located closer to the carboxy terminus relative to the epitope between aa17 and aa59. Data presented above suggest that the N epitope located between aa17 and aa59 may be a dominant epitope that is responsible for the cross-reactivity of FCV N antibodies with PHV N and Puumala virus N proteins.

C. Seroreactivity to the dominant epitope of FCV N protein.

Reactivity is specific for FCV infection. Serum samples obtained from 128 control subjects were tested for IgG antibody reactivities to the FCV N and G1 proteins. In contrast to the HPS cases above, only one of the control serum samples (0.8%) contained antibodies to both the FCV N and FCV G1 recombinant proteins. Nine of 128 control serum samples (7%) contained antibodies that reacted with the FCV N protein. The N antibody reactivities present among the control subjects mapped to an antigen site that was different from the epitope recognized by confirmed FCV-induced antibodies. Therefore, it unlikely that the N reactivities present among controls resulted from remote unrecognized FCV infections. These N reactivities may represent cross-reactive antibodies induced by infection with a different, perhaps uncharacterized, hantavirus. It is more likely that they represent antibodies induced by an irrelevant antigen that fortuitously cross-reacts with an epitope in the FCV N protein. The observation that these antibodies recognize an epitope that is different from the dominant N epitope recognized by FCV-induced antibodies provides a means for differentiating true positive FCV N antibody reactivities from false positive reactivities.

D. G1 Protein Mapping

The location of the carboxy-terminal boundary of the dominant epitope specified by the protein product of the 1275 nt FCV G1 gene clone has been determined to within 23 amino acids. The carboxy terminus of the epitope was mapped by preparing a nested series of deletions of the 3' end of the FCV insert of p3H226 G1 1275 pATH-1. A similar approach was used to prepare a series of 5' deletions of the p3H226 G1 1275 pATH-1 insert. The latter series was prepared to allow the mapping of the amino-terminal boundary of the G1 protein epitope. FCV G1-reactive antibodies reacted with the p3H226 -M-NEx222 protein (aa59–aa452) and did not react with the p3H226 -M-NEx 297 protein (aa84–aa452). All amino-to-carboxy terminus deletion constructs that were deleted beyond amino acid coordinate 84 did not react with the FCV G1-reactive antibodies. Therefore, the amino terminus boundary of the type-specific epitope(s) lies between amino acid coordinates 59 and 84. Taken in conjunction with the mapping data from the carboxy-terminal deletion series presented above, G1 immunoreactivity was localized to a single segment between aa59 and aa89 (the amino acid sequence coordinates are given in terms of the homologous positions in the sequence of Prospect Hill virus). This polypeptide segment has the amino acid sequence LKIESSDNFDLHVPATTTQKYNQVDWTKKSS (SEQ. ID NO:9). This sequence is divergent from the homologous regions of Prospect Hill virus (LKLESSCNFDVHTSSATQQAVTKWTWEKKAD) (SEQ. ID NO.84) and Puumala virus (LKLESSCNFDLHTSTAGQQSFTKWTWEIKGD) (SEQ. ID NO:85). The degree of amino acid sequence variation within this segment is consistent with the observation that FCV G1-reactive antibodies fail to cross-react with homologous regions of the G1 proteins of PHV and Puumala virus.

In the following claims, the term "protein" includes protein fragments (oligopeptides) . The claimed sequences include sequences with variations or modifications which do not substantially adversely affect the properties of the products for their intended use. Artifacts of peptide synthesis are exemplary.

The coordinate given in the claims use PHV coordinates beginning at the initiating methionine of PHV.

SEQUENCE LISTING ( 1 ) GENERAL INFORMATION:

( i i i ) NUMBER OF SEQUENCES:85

( 2 ) INFORMATION FOR SEQ ID NO:1:

( i ) SEQUENCE CHARACTERISTICS:
( A ) LENGTH: 46 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 46

( x i ) SEQUENCE DESCRIPTION: SEQ ID NO:1:

AAGATGGAAG TGATTCACGG CCTCTCTTCC CCAATGGCTC ATGTAT 46

( 2 ) INFORMATION FOR SEQ ID NO:2:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah -continued Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 30

( x i ) SEQUENCE DESCRIPTION: SEQ ID NO:2:

T A C C A A A A C T   C T G G T C A T A G   G C C A T G T A T T   3 0

( 2 ) INFORMATION FOR SEQ ID NO:3:

( i ) SEQUENCE CHARACTERISTICS:
( A ) LENGTH: 70 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 70

( x i ) SEQUENCE DESCRIPTION: SEQ ID NO:3:

G T C C T T A A G C   A A T G G T G T A C   A A C A T C A T G T   G T G T T T G G A G   A C C C C G G T G A   T A T T G T G T C A   6 0

A C G A C A A G T G   7 0

( 2 ) INFORMATION FOR SEQ ID NO:4:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 60

( x i ) SEQUENCE DESCRIPTION: SEQ ID NO:4:

GGTTTAGGTC AGGGTTACGT GACAGGTTCA GTGGAAACTA CACCTATTCT CTTAACGCAG 60

( 2 ) INFORMATION FOR SEQ ID NO:5:

( i ) SEQUENCE CHARACTERISTICS:
( A ) LENGTH: 62 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: MHAR ( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 62

( i x ) SEQUENCE DESCRIPTION: SEQ ID NO:5:

GTAGGTTTCA CATTGGTATG TACTGTAGGG CTAACAGAAT GTGCAAATTT TATAACTTCA 60

AT 62

-continued ( 2 ) INFORMATION FOR SEQ ID NO:6:

( i ) SEQUENCE CHARACTERISTICS:
( A ) LENGTH: 43
( B ) TYPE: amino acid
( C ) STRANDEDNESS: single
( D ) TOPOLOGY: linear ( i i ) MOLECULE TYPE:

( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 43

( x i ) SEQUENCE DESCRIPTION: SEQ ID NO:6:

```
Gln Leu Val Thr Ala Arg Gln Lys Leu Lys Asp Ala Glu Arg Ala
                  5                  10                  15

Val Glu Leu Asp Pro Asp Asp Val Asn Lys Ser Thr Leu Gln Ser
                 20                  25                  30

Arg Arg Ala Ala Val Ser Ala Leu Gly Thr Lys Leu Gly
                 35                  40
```

( 2 ) INFORMATION FOR SEQ ID NO:7:

( i ) SEQUENCE CHARACTERISTICS:
( A ) LENGTH: 43
( B ) TYPE: amino acid
( C ) STRANDEDNESS: single
( D ) TOPOLOGY: linear ( i i ) MOLECULE TYPE:

( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven

-continued

Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 43

( x i ) SEQUENCE DESCRIPTION: SEQ ID NO:7:

```
Gln Leu Val Ile Ala Arg Gln Lys Leu Lys Glu Ala Glu Arg Thr
                5                   10                  15

Val Glu Val Asp Pro Asp Asp Val Asn Lys Ser Thr Leu Gln Ser
                20                  25                  30

Arg Arg Ser Ala Val Ser Thr Leu Glu Asp Lys Leu Ala
                35                  40
```

( 2 ) INFORMATION FOR SEQ ID NO:8:

( i ) SEQUENCE CHARACTERISTICS:
( A ) LENGTH: 43
( B ) TYPE: amino acid
( C ) STRANDEDNESS: single
( D ) TOPOLOGY: linear ( i i ) MOLECULE TYPE:

( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 43

( x i ) SEQUENCE DESCRIPTION: SEQ ID NO:8:

```
Gln Leu Val Val Ala Arg Gln Lys Leu Lys Asp Ala Glu Arg Ala
                5                   10                  15

Val Glu Val Tyr Pro Asp Asp Val Asn Lys Asn Thr Leu Gln Ala
                20                  25                  30

Arg Gln Gln Thr Val Ser Ala Leu Glu Asp Lys Leu Ala
                35                  40
```

( 2 ) INFORMATION FOR SEQ ID NO:9:

( i ) SEQUENCE CHARACTERISTICS:
( A ) LENGTH: 31
( B ) TYPE: amino acid
( C ) STRANDEDNESS: single
( D ) TOPOLOGY: linear ( i i ) MOLECULE TYPE:

( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 31

( x i ) SEQUENCE DESCRIPTION: SEQ ID NO:9:

```
Leu Lys Ile Glu Ser Ser Asp Asn Phe Asp Leu His Val Pro Ala
                  5                  10                  15

Thr Thr Thr Gln Lys Tyr Asn Gln Val Asp Trp Thr Lys Lys Ser
                 20                  25                  30

Ser
```

( 2 ) INFORMATION FOR SEQ ID NO:10:

( i ) SEQUENCE CHARACTERISTICS:
( A ) LENGTH: 26
( B ) TYPE: amino acid
( C ) STRANDEDNESS: single
( D ) TOPOLOGY: linear ( i i ) MOLECULE TYPE:

( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: MHAR ( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi Nolte, Kurt
                    Zumwalt, Ross
                    MacInnes, Kersti
                    Myers, Gerald
            ( B ) TITLE: A Novel Hantavirus Associated with an Outbreak of
                    Fatal Respiratory Disease in the Southwestern United
                    States: Evolutionary Relationships to Known
                    Hantaviruses- Running Title: Hantavirus-associated ARDS
            ( C ) JOURNAL: Journal of Virology
            ( D ) VOLUME: 68
            ( F ) PAGES: in press
            ( G ) DATE: 1994
            ( K ) RELEVANT RESIDUES IN SEQ ID NO:1:FROM 1 TO 26

( i x ) SEQUENCE DESCRIPTION: SEQ ID NO:10:

Ser Cys Asn Phe Asp Leu His Val Pro Ala Thr Thr Thr Gln Lys
                 5                   10                  15
Tyr Asn Gln Val Asp Trp Thr Lys Lys Ser Ser
                 20                  25

( 2 ) INFORMATION FOR SEQ ID NO:11:

( i ) SEQUENCE CHARACTERISTICS:
                ( A ) LENGTH: 31
                ( B ) TYPE: amino acid
                ( C ) STRANDEDNESS: single
                ( D ) TOPOLOGY: linear ( i i ) MOLECULE TYPE:

( i i i ) HYPOTHETICAL: no ( i v ) ANTI-SENSE: no ( v ) ORIGINAL SOURCE:
                ( A ) ORGANISM: Four Corners Hantavirus
                ( C ) INDIVIDUAL ISOLATE: 3H226

( v i i ) IMMEDIATE SOURCE:
                ( A ) LIBRARY:
                ( B ) CLONE:

( x ) PUBLICATION INFORMATION:
                ( A ) AUTHORS: Hjelle, Brian
                    Jenison, Steven
                    Torrez- Martinez, Norah
                    Yamada, Takashi
                    Nolte, Kurt
                    Zumwalt, Ross
                    MacInnes, Kersti
                    Myers, Gerald
            ( B ) TITLE: A Novel Hantavirus Associated with an Outbreak of
                    Fatal Respiratory Disease in the Southwestern United
                    States: Evolutionary Relationships to Known
                    Hantaviruses- Running Title: Hantavirus-associated ARDS
            ( C ) JOURNAL: Journal of Virology
            ( D ) VOLUME: 68
            ( F ) PAGES: in press
            ( G ) DATE: 1994
            ( K ) RELEVANT RESIDUES IN SEQ ID NO:1:FROM 1 TO 31

( x i ) SEQUENCE DESCRIPTION: SEQ ID NO:11:

Leu Lys Ile Glu Ser Ser Asp Asn Phe Asp Leu His Val Pro Ala
                 5                   10                  15
Thr Thr Thr Gln Lys Tyr Asn Gln Val Asp Trp Thr Lys Lys Ser
                 20                  25                  30
Ser ( 2 ) INFORMATION FOR SEQ ID NO:12:

( i ) SEQUENCE CHARACTERISTICS:
                ( A ) LENGTH: 26
                ( B ) TYPE: amino acid ( C ) STRANDEDNESS: single
( D ) TOPOLOGY: linear ( i i ) MOLECULE TYPE:

( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: MHAR ( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 26

( i x ) SEQUENCE DESCRIPTION: SEQ ID NO:12:

```
Ser Cys Asn Phe Asp Leu His Val Pro Ala Thr Thr Thr Gln Lys
                 5                  10                  15

Tyr Asn Gln Val Asp Trp Thr Lys Lys Ser Ser
                20                  25
```

( 2 ) INFORMATION FOR SEQ ID NO:13:

( i ) SEQUENCE CHARACTERISTICS:
( A ) LENGTH: 76 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: MHAR ( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS ( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 76

( i x ) SEQUENCE DESCRIPTION: SEQ ID NO:13:

```
TCTTGTAATT TCGATCTGCA TGTCCCGGCT ACTACTACCC AAAAATACAA TCAGGTTGAC    60

TGGACCAAAA AAAGTT                                                    76
```

( 2 ) INFORMATION FOR SEQ ID NO:14:

( i ) SEQUENCE CHARACTERISTICS:
( A ) LENGTH: 76 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: MHAR ( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 76

( i x ) SEQUENCE DESCRIPTION: SEQ ID NO:14:

```
TCTTGTAATT TCGATCTGCA TGTCCCGGCT ACTACTACCC AAAAATACAA TCAGGTTGAC    60

TGGACCAAAA AAAGTT                                                    76
```

( 2 ) INFORMATION FOR SEQ ID NO:15:

( i ) SEQUENCE CHARACTERISTICS:
( A ) LENGTH: 26
( B ) TYPE: amino acid
( C ) STRANDEDNESS: single
( D ) TOPOLOGY: linear ( i i ) MOLECULE TYPE:

( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:

( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 26

( x i ) SEQUENCE DESCRIPTION: SEQ ID NO:15:

Ser Cys Asn Phe Asp Leu His Val Pro Ala Thr Thr Thr Gln Lys
5 10 15

Tyr Asn Gln Val Asp Trp Thr Lys Lys Ser Ser
20 25

( 2 ) INFORMATION FOR SEQ ID NO:16:

( i ) SEQUENCE CHARACTERISTICS:
( A ) LENGTH: 70
( B ) TYPE: amino acid
( C ) STRANDEDNESS: single
( D ) TOPOLOGY: linear ( i i ) MOLECULE TYPE:

( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 70

( x i ) SEQUENCE DESCRIPTION: SEQ ID NO:16:

Met Ser Thr Leu Lys Glu Val Gln Asp Asn Ile Thr Leu His Glu
5 10 15

Gln Gln Leu Val Thr Ala Arg Gln Lys Leu Lys Asp Ala Glu Arg
20 25 30

-continued

Ala Val Glu Leu Asp Pro Asp Asp Val Asn Lys Ser Thr Leu Gln
35 40 45

Ser Arg Arg Ala Ala Val Ser Ala Leu Glu Thr Lys Leu Gly Glu
50 55 60

Leu Lys Arg Glu Leu Ala Asp Leu Ile Ala
65 70

( 2 ) INFORMATION FOR SEQ ID NO:17:

( i ) SEQUENCE CHARACTERISTICS:
( A ) LENGTH: 43
( B ) TYPE: amino acid
( C ) STRANDEDNESS: single
( D ) TOPOLOGY: linear ( i i ) MOLECULE TYPE:

( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 43

( x i ) SEQUENCE DESCRIPTION: SEQ ID NO:17:

Gln Leu Val Thr Ala Arg Gln Lys Leu Lys Asp Ala Glu Arg Ala
5 10 15

Val Glu Leu Asp Pro Asp Asp Val Asn Lys Ser Thr Leu Gln Ser
20 25 30

Arg Arg Ala Ala Val Ser Ala Leu Glu Thr Lys Leu Gly
35 40

( 2 ) INFORMATION FOR SEQ ID NO:18:

( i ) SEQUENCE CHARACTERISTICS:
( A ) LENGTH: 1068 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: MHAR -continued ( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 1068

( i x ) SEQUENCE DESCRIPTION: SEQ ID NO:18:

```
AGCACATTAC AGAGCAGACG GGCAGCTGTG TCTGCATTGG AGACCAAACT CGGAGAACTC      60
AAGCGGGAAC TGGCTGATCT TATTGCAGCT CAGAAATTGG CTTCAAAACC TGTTGATCCA     120
ACAGGGATTG AACCTGATGA CCATTTAAAG GAAAAATCAT CACTGAGATA TGGAAATGTC     180
CTTGATGTAA ATTCCATTGA CCTAGAAGAA CCAAGTGGGC AAACAGCTGA TTGGAAATCC     240
ATCGGACTCT ACATTCTAAG TTTTGCATTA CCGATTATCC TTAAAGCCTT GTACATGTTA     300
TCTACTAGAG GCCGTCAAAC AATCAAAGAA AACAAGGGAA CAAGAATTCG ATTTAAGGAT     360
GATTCATCTT ATGAAGAAGT CAATGGAATA CGTAAACCAA GACATCTATA TGTTTCTATG     420
CCAACTGCTC AGTCTACAAT GAAAGCAGAT GAGATTACTC CTGGGAGGTT CCGTACAATT     480
GCTTGTGGGT TATTCCCGGC CCAAGTCAAA GCAAGGAATA TTATCAGTCC TGTTATGGGT     540
GTGATTGGCT TTAGTTTCTT TGTGAAAGAT TGGATGGAAA GAATTGATGA CTTTCTGGCT     600
GCACGTTGTC CATTTCTACC CGAACAGAAA GACCCTAGGG ATGCTGCATT GGCAACTAAC     660
AGAGCCTATT TTATAACACG TCAATTACAG GTTGATGAGT CAAAGGTTAG TGATATTGAG     720
GATCTAATTG CTGATGCAAG GGCTGAGTCT GCCACTATAT TCGCAGATAT CGCCACTCCT     780
CATTCAGTTT GGGTCTTCGC ATGTGCTCCA GATCGTTGTC CACCTACAGC ATTATATGTG     840
GCCGGGATGC CGGAGTTGGG TGCATTTTTT GCTATTCTTC AGGATATGAG GAACACCATA     900
ATGGCATCAA AATCTGTGGG GACATCTGAA GAGAAATTGA AGAAAAAATC AGCATTCTAC     960
CAGTCATACT TGAGACGTAC TCAGTCAATG GGGATTCAAC TGGACCAGAA GATAATCATC    1020
TTATACATGA GCCATTGGGG AAGAGAGGCC GTCAATCACT TCCATCTT                 1068
```

( 2 ) INFORMATION FOR SEQ ID NO:19:

( i ) SEQUENCE CHARACTERISTICS:
( A ) LENGTH: 1224 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: MHAR ( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 1224

( i x ) SEQUENCE DESCRIPTION: SEQ ID NO:19:

GGTTTAGCTC AGGGTTACGT GACAGGTTCA GTGGAAACTA CACCTATTCT CTTAACGCAG 60

GTAGCTGATC TTAAGATTGA GAGTTCTTGT AATTTCGATC TGCATGTCCC GGCTACTACT 120

ACCCAAAAAT ACAATCAGGT TGACTGGACC AAAAAAAGTT CAACTACAGA AAGCACAAAT 180

GCAGGTGCAA CTACATTTGA GGCTAAAACA AAAGAGATAA ATTTAAAAGG CACATGTAAT 240

ATTCTTCCAA CTACATTTGA AGCTGCATAT AAATCAAGGA AGACAGTAAT TTGTTATGAT 300

TTAGCCTGTA ATCAAACACA TTGTCTTCCT ACAGTCCATT TGATTGCTCC TGTTCAAACG 360

TGCATGTCTG TGCGGAGCTG TATGATAGGT TTGCTGTCAA ACAGGATTCA AGTCATATAT 420

GAGAAGACAT ACTGTGTTAC AGGTCAATTA ATAGAGGGGC TATGTTTCAT CCCAACACAT 480

ACAATTGCAC TCACACAACC TGGTCATACC TATGATACTA TGACATTGCC AGTGACTTGT 540

TTTTTAGTAG CTAAAAAGTT GGGAACACAA CTTAAGCTGG CTGTTGAGTT AGAGAAACTG 600

ATTACTGGTG TGAGTTGCAC AGAAAACAGC TTTCAAGGTT ACTACATCTG CTTTATCGGA 660

AAACATTCAG AGCCCTTATT TGTGCCAACA ATGGAAGATT ATAGGTCAGC TGAGTTATTT 720

ACCCGTATGG TTTTAAATCC GAGAGGTGAA GATCATGACC CTGATCAAAA TGGACAAGGC 780

TTAATGAGAA TAGCCGGACC TGTTACAGCT AAGGTGCCAT CTACAGAAAC TGGACAAGGC 840

ATGCAAGGAA TTGCATTTGC TGGGGCACCG ATGTATAGCT CTTTCTCAAC TCTCGTGAGG 900

AAGGCTGATC CTGAGTATGT CTTCTCCCCA GGTATAATTG CAGAATCAAA TCATAGTGTC 960

TGTGATAAGA AAACAGTACC CCTTACATGG ACAGGGTTTT TGGCAGTTTC TGGAGAGATA 1020

GAGAAAATAA CAGGCTGTAC AGTCTTCTGT ACATTGGCAG GACCTGGTGC TAGTTGTGAA 1080

GCATACTCAG AAACAGGAAT CTTTAATATA AACTTCATGT GCCAAAGAGT GAATAAAGTT 1140

CAAAAATTCA GAGGCTCAGA ACAGAGAATC AACTTCATGT GCCAAAGAGT TGATCAAGAT 1200

GTTGTAGTCT ATTGTAATGG GCAA 1224

( 2 ) INFORMATION FOR SEQ ID NO:20:

( i ) SEQUENCE CHARACTERISTICS:
( A ) LENGTH: 1191 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no -continued ( i v ) ANTI-SENSE: no ( v ) ORIGINAL SOURCE:
( A ) ORGANISM: Four Corners Hantavirus
( C ) INDIVIDUAL ISOLATE: MHAR ( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 1191

( i x ) SEQUENCE DESCRIPTION: SEQ ID NO:20:

ATGAGCACCC TCAAAGAAGT GCAAGACAAC ATTACTCTCC ACGAACAACA ACTTGTGACT 60

GCCAGGCAGA AGCTCAAAGA TGCAGAAAGA GCGGTGGAAT TGGACCCCGA TGATGTTAAC 120

AAAAGCACAT TACAGAGCAG ACGGGCAGCT GTGTCTGCAT TGGAGACCAA ACTCGGAGAA 180

CTCAAGCGGG AACTGGCTGA TCTTATTGCA GCTCAGAAAT TGGCTTCAAA ACCTGTTGAT 240

CCAACAGGGA TTGAACCTGA TGACCATTTA AAGGAAAAAT CATCACTGAG ATATGGAAAT 300

GTCCTTGATG TAAATTCCAT TGACCTCGAG GAACCAAGTG GGCAAACAGC TGATTGGAAA 360

TCCATCGGAC TCTACATTCT AAGTTTTGCA TTACCGATTA TCCTTAAAGC CTTGTACATG 420

TTATCTACTA GAGGCCGTCA AACAATCAAA GAAAACAAGG GAACAAGAAT TCGATTTAAG 480

GATGATTCAT CTTATGAAGA AGTCAATGGA ATACGTAAAC CAAGACATCT ATATGTTTCT 540

ATGCCAACTG CTCAGTCTAC AATGAAAGCA GATGAGATTA CTCCTGGGAG GTTCCGTACA 600

ATTGCTTGTG GGTTATTCCC GGCCCAAGTC AAAGCAAGGA ATATTATCAG TCCTGTTATG 660

GGTGTGATTG GCTTTAGTTT CTTTGTGAAA GATTGGATGG AAAGAATTGA TGACTTTCTG 720

GCTGCACGTT GTCCATTTCT ACCCGAACAG AAAGACCCTA GGGATGCTGC ATTGGCAACT 780

AACAGAGCCT ATTTTATAAC ACGTCAATTA CAGGTTGATG AGTCAAAGGT TAGTGATATT 840

GAGGATCTAA TTGCTGATGC AAGGGCTGAG TCTGCCACTA TATTCGCAGA TATCGCCACT 900

CCTCATTCAG TTTGGGTCTT CGCATGTGCT CCAGATCGTT GTCCACCTAC AGCATTATAT 960

GTGGCCGGGA TGCCGGAGTT GGGTGCATTT TTTGCTATTC TTCAGGATAT GAGGAACACC 1020

ATAATGGCAT CAAAATCTGT GGGGACATCT GAAGAGAAAT TGAAGAAAAA ATCAGCATTC 1080

TACCAGTCAT ACTTGAGACG TACTCAGTCA ATGGGGATTC AACTGGACCA GAAGATAATC 1140

ATCTTATACA TGAGCCATTG GGGAAGAGAG GCCGTGAATC ACTTCCATCT T 1191

( 2 ) INFORMATION FOR SEQ ID NO:21:

( i ) SEQUENCE CHARACTERISTICS:
( A ) LENGTH: 330 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 330

( x i ) SEQUENCE DESCRIPTION: SEQ ID NO:21:

```
ATGAGCACCC TCAAAGAAGT GCAAGACAAC ATTACTCTCC ACGAACAACA ACTTGTGACT    60

GCCAGGCAGA AGCTCAAAGA TGCAGAAAGA GCGGTGGAAT TGGACCCCGA TGATGTTAAC   120

AAAAGCACAT TACAGAGCAG ACGGGCAGCT GTGTCTGCAT TGGAGACCAA ACTCGGAGAA   180

CTCAAGCGGG AACTGGCTGA TCTTATTGCA GCTCAGAAAT TGGCTTCAAA ACCTGTTGAT   240

CCAACAGGGA TTGAACCTGA TGACCATTTA AAGGAAAAAT CATCACTGAG ATATGGAAAT   300

GTCCTTGATG TAAATTCCAT TGACCTCGAG                                    330
```

( 2 ) INFORMATION FOR SEQ ID NO:22:

( i ) SEQUENCE CHARACTERISTICS:
( A ) LENGTH: 109
( B ) TYPE: amino acid
( C ) STRANDEDNESS: single
( D ) TOPOLOGY: linear ( i i ) MOLECULE TYPE:

( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald -continued ( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 109

( x i ) SEQUENCE DESCRIPTION: SEQ ID NO:22:

```
Met Ser Thr Leu Lys Glu Val Gln Asp Asn Ile Thr Leu His Glu
                  5                  10                  15

Gln Gln Leu Val Thr Ala Arg Gln Lys Leu Lys Asp Ala Glu Arg
                 20                  25                  30

Ala Val Glu Leu Asp Pro Asp Asp Val Asn Lys Ser Thr Leu Gln
                 35                  40                  45

Ser Arg Arg Ala Ala Val Ser Ala Leu Glu Thr Lys Leu Gly Glu
                 50                  55                  60

Leu Lys Arg Glu Leu Ala Asp Leu Ile Ala Ala Gln Lys Leu Ala
                 65                  70                  75

Ser Lys Pro Val Asp Pro Thr Gly Ile Glu Pro Asp Asp His Leu
                 80                  85                  90

Lys Glu Lys Ser Ser Leu Arg Tyr Gly Asn Val Leu Val Val Asn
                 95                 100                 105

Ser Ile Asp Leu
```

( 2 ) INFORMATION FOR SEQ ID NO:23:

( i ) SEQUENCE CHARACTERISTICS:
( A ) LENGTH: 3351 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 3351

( x i ) SEQUENCE DESCRIPTION: SEQ ID NO:23:

```
TAGTAGTAGA CTCCGCAAGA AGAAGCAAAC ACTGAATAAA GGAGATACAG AATGGTAGGG     60
```

-continued

```
TGGGTTTGCA TCTTCCTCGT GGTCCTTACT ACTGCAACTG CTGGGCTAAC ACGGAATCTT    120
TATGAGTTGA AGATAGAATG TCCACATACT GTAGGTTTAG GTCAGGGTTA CGTGACAGGT    180
TCAGTGGAAA CTACACCTAT TCTCTTAACG CAGGTAGCTG ATCTTAAGAT TGAGAGTTCT    240
TGTAATTTCG ATCTGCATGT CCCGGCTACT ACTACCCAAA AATACAATCA GGTTGACTGG    300
ACCAAAAAAA GTTCAACTAC AGAAAGCACA AATGCAGGTG CAACTACATT TGAGGCTAAA    360
ACAAAAGAGA TAAATTTAAA AGGCACATGT AATATTCCTC CAACTACATT TGAAGCTGCA    420
TATAAATCAA GGAAGACAGT AATTTGTTAT GATTTAGCCT GTAATCAAAC ACATTGTCTT    480
CCTACAGTCC ATTTGATTGC TCCTGTTCAA ACGTGCATGT CTGTGCGGAG CTGTATGATA    540
GGTTTGCTGT CAAGCAGGAT TCAAGTCATA TATGAGAAGA CATACTGTGT TACAGGTCAA    600
TTAATAGAGG GGCTATGTTT CATCCCAACA CATACAATTG CACTCACACA ACCTGGTCAT    660
ACCTATGATA CTATGACATT GCCAGTGACT TGTTTTTTAG TAGCTAAAAA GTTGGGAACA    720
CAACTTAAGC TGGCTGTTGA GTTAGAGAAA CTGATTACTG GTGTGAGTTG CACAGAAAAC    780
AGCTTTCAAG GTTACTACAT CTGCTTTATC GGAAAACATT CAGAGCCCTT ATTTGTGCCA    840
ACAATGGAAG ATTATAGGTC AGCTGAGTTA TTTACCCGTA TGGTTTTAAA TCCGAGAGGT    900
GAAGATCATG ACCCTGATCA AAATGGACAA GGCTTAATGA GAATAGCCGG ACCTGTTACA    960
GCTAAGGTGC CATCTACAGA AACAACGGAA ACAATGCAAG GAATTGCATT TGCTGGGGCA   1020
CCGATGTATA GCTCTTTCTC AACTCTCGTG AGGAAGGCTG ATCCTGAGTA TGTCTTCTCC   1080
CCAGGTATAA TTGCAGAATC AAATCATAGT GTCTGTGATA AGAAAACAGT ACCCCTTACA   1140
TGGACAGGGT TTTTGGCAGT TTCTGGAGAG ATAGAGAAAA TAACAGGCTG TACAGTCTTC   1200
TGTACATTGG CAGGACCTGG TGCTAGTTGT GAAGCATACT CAGAAACAGG AATCTTTAAT   1260
ATAAGCTCTC CTACTTGTTT GGTGAATAAA GTTCAAAAAT TCAGAGGCTC AGAACAGAGA   1320
ATCAACTTCA TGTGCCAAAG AGTTGATCAA GATGTTGTAG TCTATTGTAA TGGGCAAAAG   1380
AAAGTCATTC TTACCAAAAC TCTGGTCATA GGCCAATGTA TTTATACATT CACTAGTTTA   1440
TTCTCACTAA TCCTAGGAGT TGCCCATTCT CTTGCCGTAG AGCTATGTGT TCCAGGTCTT   1500
CATGGCTGGG CTACAACAGC ATTACTGATT ACTTTTTGCT TTGGCTGGCT CCTTATACCG   1560
ACAGTCACCT TAATTATACT AAAGATCCTG AGGTTGCTCA CTTTCTCATG CTCACATTAT   1620
TCTACAGAAT CAAAATTCAA AGTTATCTTA GAAAGAGTTA AGGTTGAATA CCAAAAAACA   1680
ATGGGCTCTA TGGTGTGTGA TATTTGCCAC CATGAATGCG AAACAGCAAA AGAACTTGAA   1740
ACACATAAGA AAAGCTGTCC AGAAGGTCAA TGCCCGTATT GTATGACAAT AACTGAATCC   1800
ACTGAGATGG CTCTTCAAGC CCATTTTGCA ATCTGTAAGT TAACAAACAG GTTTCAGGAA   1860
AACTTAAAAA AATCATTAAA ACGCCCAGAA GTACGGAAAG GTTGTTACAG GACACTGGGA   1920
GTTTTTAGAT ACAAGAGCAG ATGTTATGTT GGTTTAGTAT GGGGAATTCT TTTAACAACT   1980
GAACTGATCA TATGGGCAGC CAGTGCAGAA ACCCCCTTAA TGGAGTCTGG TTGGTCTGAC   2040
ACAGCGCATG GTGTGGGCAT AATTCCTATG AAGACAGATT TGGAGCTTGA CTTTGCATCG   2100
GCCTCATCAT CTTCTTACAG TTATAGGCGA AAGCTTATAA ACCCTGCTAA TCAAGAAGAA   2160
ACACTCCCTT TTCATTTCCA GTTAGACAAA CAAGTAGTGC ATGCAGAGAT CCAGAACCTA   2220
GGACATTGGA TGGATGGTAC ATTCAACATA AAAACTGCTT TTCACTGTTA TGGGGAGTGT   2280
AAAAAATATG CCTATCCTTG GCAAACAGCC AAGTGCTTCT TTGAAAAGGA TTATCAGTAT   2340
GAAACAAGTG GGGGCTGTAA TCCACCAGAC TGTCCAGGGG TAGGTACAGG TTGTACAGCT   2400
TGTGGGGTGT ATCTCGATAA GTCCCGTTCG GTTGGGAAAG CATACAAGAT AGTATCACTC   2460
```

-continued

```
AAATACACAC GGAAGGTGTG TATTCAATTA AGGAACAGAA AAACTTGTAA ACATATAGAT   2520
GTAAATGATT GCTTGGTTAC CCCTTCTGTC AAAGTTTGTA TGATCGGTAC TATATCAAAG   2580
CTCCAACCAG GTGATACTTT GTTGTTCTTA GGCCCTTTAG AGCAGGGTGG GATTATCCTT   2640
AAGCAATGGT GTACAACATC ATGTGTGTTT GGAGACCCCG GTGATATTAT GTCAACGACA   2700
AGTGGGATGA GGTGCCCAGA ACATACTGGA TCTTTTAGAA AGATATGTGG GTTTGCTACA   2760
ACACCAACAT GTGAGTATCA AGGCAACACA GTGTCTGGGT TCAAACGCAT GATGGCAACT   2820
CGAGATTCTT TCCAATCATT CAATGTGACA GAACCACATA TCACTAGCAA CCGACTTGAG   2880
TGGATTGATC CAGATAGCAG TATCAAAGAT CATATTAATA TGGTTTTAAA TCGGGATGTT   2940
TCCTTTCAGG ATCTAAGTGA TAACCCATGC AAGGTTGATC TGCATATACA ATCAATTGAT   3000
GGGGCCTGGG GTTCAGGGGT AGGTTTTACG TTGGTATGCA CTGTGGGGCT TACAGAGTGT   3060
GCAAATTTTA TAACTTCAAT TAAAGCATGT GATTCTGCCA TGTGTTATGG AGCCACAGTG   3120
ACAAATCTGC TTAGAGGGTC AAACACAGTT AGAGTTGTTG GTAAAGGTGG GCATTCTGGA   3180
TCTTTGTTTA AATGCTGCAA TGATACTGAC TGTACCGAAG AAGGTTTAGC AGCATCTCCA   3240
CCACATTTAG ATAGGGTTAC AGGTCACAAT CAAATAGATT CTGATAAAGT TTATGATGAC   3300
GTTGCACCGC CCTGTACAAT CAAGTGTTGG TTTAAAAAAT CTGGGGAATG G            3351
```

( 2 ) INFORMATION FOR SEQ ID NO:24:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 23

( x i ) SEQUENCE DESCRIPTION: SEQ ID NO:24:

```
TAGTAGTAGA CTCCGCAAGA AGA                                           23
```

( 2 ) INFORMATION FOR SEQ ID NO:25:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 23

( x i ) SEQUENCE DESCRIPTION: SEQ ID NO:25:

TAGTAGTAGA CTCCGCAAGA AGA 23

( 2 ) INFORMATION FOR SEQ ID NO:26:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology ( D ) VOLUME: 68
( F ) PAGES: in press
( G ) DATE: 1994
( K ) RELEVANT RESIDUES IN SEQ ID NO:1:FROM 1 TO 23

( x i ) SEQUENCE DESCRIPTION: SEQ ID NO:26:

TAGTAGTAGA CTCCGCAAGA AGA 23

( 2 ) INFORMATION FOR SEQ ID NO:27:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 23

( x i ) SEQUENCE DESCRIPTION: SEQ ID NO:27:

AGATTGAATG TCCTCATACT GTA 23

( 2 ) INFORMATION FOR SEQ ID NO:28:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian

-continued

Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 23

( x i ) SEQUENCE DESCRIPTION: SEQ ID NO:28:

AAATGGAATG TCCACATACT ATT 23

( 2 ) INFORMATION FOR SEQ ID NO:29:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 24

( x i ) SEQUENCE DESCRIPTION: SEQ ID NO:29:

ACCATGGAAT GTCCTCATAC TGTA 24

( 2 ) INFORMATION FOR SEQ ID NO:30:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 24

( x i ) SEQUENCE DESCRIPTION: SEQ ID NO:30:

TGTGTACTGT AATGGCATGA AGAA 24

( 2 ) INFORMATION FOR SEQ ID NO:31:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 24

( x i ) SEQUENCE DESCRIPTION: SEQ ID NO:31:

TGTTTACTGT AATGGGATGA AGAA 24

( 2 ) INFORMATION FOR SEQ ID NO:32:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 26

( x i ) SEQUENCE DESCRIPTION: SEQ ID NO:32:

TGTGTTACTG TAATGGCGAT GAAGAA 26

( 2 ) INFORMATION FOR SEQ ID NO:33:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known -continued Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 26

( x i ) SEQUENCE DESCRIPTION: SEQ ID NO:33:

AAGAAGGTAA TTCTTACTAA AACCCT 26

( 2 ) INFORMATION FOR SEQ ID NO:34:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 26

( x i ) SEQUENCE DESCRIPTION: SEQ ID NO:34:

AAGAAAGTCA TTCTCACCAA GACCCT 26

( 2 ) INFORMATION FOR SEQ ID NO:35:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

-continued ( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 28

( x i ) SEQUENCE DESCRIPTION: SEQ ID NO:35:

AAGAAGAGTA CATTCTTACT AAAACCCT 28

( 2 ) INFORMATION FOR SEQ ID NO:36:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 18

( x i ) SEQUENCE DESCRIPTION: SEQ ID NO:36:

ACATTCTGTT TTGGCTGG 18

( 2 ) INFORMATION FOR SEQ ID NO:37:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 18

( x i ) SEQUENCE DESCRIPTION: SEQ ID NO:37:

ACATTCTGTT TTGGCTGG 18

( 2 ) INFORMATION FOR SEQ ID NO:38:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 18

( x i ) SEQUENCE DESCRIPTION: SEQ ID NO:38:

ACATTCTGTT TTGGCTGG 18

( 2 ) INFORMATION FOR SEQ ID NO:39:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 21

( x i ) SEQUENCE DESCRIPTION: SEQ ID NO:39:

A T G G T C T G T G A G G T T T G T C A G 2 1

( 2 ) INFORMATION FOR SEQ ID NO:40:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 21

( x i ) SEQUENCE DESCRIPTION: SEQ ID NO:40:

ATGGTTTGTG AAGTGTGTCA G 21

( 2 ) INFORMATION FOR SEQ ID NO:41:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 23

( x i ) SEQUENCE DESCRIPTION: SEQ ID NO:41:

ATGGTCTTGT GAGAGTTTGT CAG 23

( 2 ) INFORMATION FOR SEQ ID NO:42:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:

( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of
Fatal Respiratory Disease in the Southwestern United
States: Evolutionary Relationships to Known
Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 42

( x i ) SEQUENCE DESCRIPTION: SEQ ID NO:42:

TTTAGAAAGA AATGTGCATT TGC 23

( 2 ) INFORMATION FOR SEQ ID NO:43:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of
Fatal Respiratory Disease in the Southwestern United
States: Evolutionary Relationships to Known
Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 23

( x i ) SEQUENCE DESCRIPTION: SEQ ID NO:43:

TTTAGAAAGA AATGTGCATT TGC 23

( 2 ) INFORMATION FOR SEQ ID NO:44:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 23

( x i ) SEQUENCE DESCRIPTION: SEQ ID NO:44:

TTTAGAAAGA AATGTGCATT TGC 23

( 2 ) INFORMATION FOR SEQ ID NO:45:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 18

( x i ) SEQUENCE DESCRIPTION: SEQ ID NO:45:

T G G T G C A T G G   G G C T C A G G   1 8

( 2 ) INFORMATION FOR SEQ ID NO:46:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 18

( x i ) SEQUENCE DESCRIPTION: SEQ ID NO:46:

T G G A G C A T G G   G G T T C A G G   1 8

( 2 ) INFORMATION FOR SEQ ID NO:47:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 20

( x i ) SEQUENCE DESCRIPTION: SEQ ID NO:47:

T T G T A G C A T G   G G G C T T C A G G   2 0

( 2 ) INFORMATION FOR SEQ ID NO:48:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 24

( x i ) SEQUENCE DESCRIPTION: SEQ ID NO:48:

T G G T T T A A A A   A G T C T G G G G A   A T G G   2 4

( 2 ) INFORMATION FOR SEQ ID NO:49:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

(vii) IMMEDIATE SOURCE:
(A) LIBRARY:
(B) CLONE:

(x) PUBLICATION INFORMATION:
(A) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
(B) TITLE: A Novel Hantavirus Associated with an Outbreak of Fatal Respiratory Disease in the Southwestern United States: Evolutionary Relationships to Known Hantaviruses- Running Title: Hantavirus-associated ARDS
(C) JOURNAL: Journal of Virology
(D) VOLUME: 68
(F) PAGES: in press
(G) DATE: 1994
(K) RELEVANT RESIDUES IN SEQ ID NO:1:FROM 1 TO 24

(xi) SEQUENCE DESCRIPTION: SEQ ID NO:49:

TGGTTTAAAA AATCAGGTGA ATGG 24

(2) INFORMATION FOR SEQ ID NO:50:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: cDNA viral (iii) HYPOTHETICAL: no (iv) ANTI-SENSE: no (v) ORIGINAL SOURCE:
(A) ORGANISM: Four Corners Hantavirus
(C) INDIVIDUAL ISOLATE: 3H226

(vii) IMMEDIATE SOURCE:
(A) LIBRARY:
(B) CLONE:

(x) PUBLICATION INFORMATION:
(A) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
(B) TITLE: A Novel Hantavirus Associated with an Outbreak of Fatal Respiratory Disease in the Southwestern United States: Evolutionary Relationships to Known Hantaviruses- Running Title: Hantavirus-associated ARDS
(C) JOURNAL: Journal of Virology
(D) VOLUME: 68
(F) PAGES: in press
(G) DATE: 1994
(K) RELEVANT RESIDUES IN SEQ ID NO:1:FROM 1 TO 26

(xi) SEQUENCE DESCRIPTION: SEQ ID NO:50:

TGGTTTAAAA AAGTCTAGGG GAATGG 26

(2) INFORMATION FOR SEQ ID NO:51:

(i) SEQUENCE CHARACTERISTICS:
(A) LENGTH: 20 base pairs
(B) TYPE: nucleic acid
(C) STRANDEDNESS: single ( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 20

( x i ) SEQUENCE DESCRIPTION: SEQ ID NO:51:

A A T T G G A T G G   T A G T G G C A G T   2 0

( 2 ) INFORMATION FOR SEQ ID NO:52:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 20

( x i ) SEQUENCE DESCRIPTION: SEQ ID NO:52:

AATTGGATGG TTGTTGCTGT 20

( 2 ) INFORMATION FOR SEQ ID NO:53:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 22

( x i ) SEQUENCE DESCRIPTION: SEQ ID NO:53:

AATTGGATGG TATGTGTGCA GT 22

( 2 ) INFORMATION FOR SEQ ID NO:54:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 25

( x i ) SEQUENCE DESCRIPTION: SEQ ID NO:54:

TAGTAGACTT CGTAAAGAGC TACTA 25

( 2 ) INFORMATION FOR SEQ ID NO:55:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 25

( x i ) SEQUENCE DESCRIPTION: SEQ ID NO:55:

TAGTAGACTC CTTGAAAAGC TACTA 25

( 2 ) INFORMATION FOR SEQ ID NO:56:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus ( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 27

( x i ) SEQUENCE DESCRIPTION: SEQ ID NO:56:

TAGTAGACTT CTTAGAAGAA GCTACTA 27

( 2 ) INFORMATION FOR SEQ ID NO:57:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 24

( x i ) SEQUENCE DESCRIPTION: SEQ ID NO:57:

GGTGGACCCA GATGACGTTA ACAA 24

( 2 ) INFORMATION FOR SEQ ID NO:58:

( i ) SEQUENCE CHARACTERISTICS:
( A ) LENGTH: 24 base pairs ( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of
Fatal Respiratory Disease in the Southwestern United
States: Evolutionary Relationships to Known
Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 24

( x i ) SEQUENCE DESCRIPTION: SEQ ID NO:58:

AGTGGACCCG GATGACGTTA ACAA 24

( 2 ) INFORMATION FOR SEQ ID NO:59:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of
Fatal Respiratory Disease in the Southwestern United
States: Evolutionary Relationships to Known
Hantaviruses- Running Title: Hantavirus-associated ARDS
( C ) JOURNAL: Journal of Virology
( D ) VOLUME: 68
( F ) PAGES: in press ( G ) DATE: 1994
( K ) RELEVANT RESIDUES IN SEQ ID NO:1:FROM 1 TO 25

( x i ) SEQUENCE DESCRIPTION: SEQ ID NO:59:

GGTGGACCCA GGATGACGTT AACAA 25

( 2 ) INFORMATION FOR SEQ ID NO:60:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of
Fatal Respiratory Disease in the Southwestern United
States: Evolutionary Relationships to Known
Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 24

( x i ) SEQUENCE DESCRIPTION: SEQ ID NO:60:

GGTGATGATA TGGATCCCGA GCTA 24

( 2 ) INFORMATION FOR SEQ ID NO:61:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 24

( x i ) SEQUENCE DESCRIPTION: SEQ ID NO:61:

GGTGATGACA TGGATCCTGA GCTA 24

( 2 ) INFORMATION FOR SEQ ID NO:62:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 25

( x i ) SEQUENCE DESCRIPTION: SEQ ID NO:62:

GGTGATGATC ATGGATCCCG AGCTA 25

( 2 ) INFORMATION FOR SEQ ID NO:63:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 23

( x i ) SEQUENCE DESCRIPTION: SEQ ID NO:63:

AAAGAGATAT CTAACCAAGA GCC 23

( 2 ) INFORMATION FOR SEQ ID NO:64:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 23

( x i ) SEQUENCE DESCRIPTION: SEQ ID NO:64:

AAAGAGATAT CAAACCAAGA ACC 23

( 2 ) INFORMATION FOR SEQ ID NO:65:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of
Fatal Respiratory Disease in the Southwestern United
States: Evolutionary Relationships to Known
Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 24

( x i ) SEQUENCE DESCRIPTION: SEQ ID NO:65:

AAAGAGATAT CTAAACCAAG AGCC 24

( 2 ) INFORMATION FOR SEQ ID NO:66:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of
Fatal Respiratory Disease in the Southwestern United
States: Evolutionary Relationships to Known
Hantaviruses- Running Title: Hantavirus-associated ARDS
( C ) JOURNAL: Journal of Virology ( D ) VOLUME: 68
( F ) PAGES: in press
( G ) DATE: 1994
( K ) RELEVANT RESIDUES IN SEQ ID NO:1:FROM 1 TO 24

( x i ) SEQUENCE DESCRIPTION: SEQ ID NO:66:

GTTCAAAAAT TCAGAGGCTC AGAA 24

( 2 ) INFORMATION FOR SEQ ID NO:67:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 21

( x i ) SEQUENCE DESCRIPTION: SEQ ID NO:67:

CAACTTCATG TGCCAAAGAG T 21

( 2 ) INFORMATION FOR SEQ ID NO:68:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian

Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 25

( x i ) SEQUENCE DESCRIPTION: SEQ ID NO:68:

G G T G G A C C C A   G G A T G A C G T T   A A C A A   2 5

( 2 ) INFORMATION FOR SEQ ID NO:69:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 25

( x i ) SEQUENCE DESCRIPTION: SEQ ID NO:69:

T A G C T C G G G A   T C C A T A G T C A   T C A C C   2 5

( 2 ) INFORMATION FOR SEQ ID NO:70:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of
Fatal Respiratory Disease in the Southwestern United
States: Evolutionary Relationships to Known
Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 21

( x i ) SEQUENCE DESCRIPTION: SEQ ID NO:70:

C A A C T T C A T G T G C C A A A G A G T 2 1

( 2 ) INFORMATION FOR SEQ ID NO:71:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of
Fatal Respiratory Disease in the Southwestern United
States: Evolutionary Relationships to Known
Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 26

( x i ) SEQUENCE DESCRIPTION: SEQ ID NO:71:

C C A T T C C C C A T G A C T T T T T T A A A C C A 2 6

( 2 ) INFORMATION FOR SEQ ID NO:72:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 18

( x i ) SEQUENCE DESCRIPTION: SEQ ID NO:72:

A C A T T C T G T T   T T G G C T G G   1 8

( 2 ) INFORMATION FOR SEQ ID NO:73:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 22

( x i ) SEQUENCE DESCRIPTION: SEQ ID NO:73:

G C A A A T G C A C   A T T T C T T T C T   A A   2 2

( 2 ) INFORMATION FOR SEQ ID NO:74:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of
Fatal Respiratory Disease in the Southwestern United
States: Evolutionary Relationships to Known
Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 24

( x i ) SEQUENCE DESCRIPTION: SEQ ID NO:74:

A C C A T G G A A T   G T C C T C A T A C   T G T A   2 4

( 2 ) INFORMATION FOR SEQ ID NO:75:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 28

( x i ) SEQUENCE DESCRIPTION: SEQ ID NO:75:

AGGGTTTTAG TAAGAATTGA CCTTTCTT 28

( 2 ) INFORMATION FOR SEQ ID NO:76:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 20

( x i ) SEQUENCE DESCRIPTION: SEQ ID NO:76:

TGGTAGCATG GGGCTTCAGG 20

( 2 ) INFORMATION FOR SEQ ID NO:77:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 22

( x i ) SEQUENCE DESCRIPTION: SEQ ID NO:77:

ACTGCCAACT AACCATCCAA TT 22

( 2 ) INFORMATION FOR SEQ ID NO:78:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 22

( x i ) SEQUENCE DESCRIPTION: SEQ ID NO:78:

TACGACTAAG CTTATGACGA CCCTCAAAGA AG 32

( 2 ) INFORMATION FOR SEQ ID NO:79:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 33

( x i ) SEQUENCE DESCRIPTION: SEQ ID NO:79:

TGGTTCCTCG AGGTCAATGG AATTTACATC AAG 33

( 2 ) INFORMATION FOR SEQ ID NO:80:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 31

( x i ) SEQUENCE DESCRIPTION: SEQ ID NO:80:

ATTGACCTCG AGGAACCAAG TGGGCAAACA G 31

( 2 ) INFORMATION FOR SEQ ID NO:81:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 28

( x i ) SEQUENCE DESCRIPTION: SEQ ID NO:81:

GGCTTCTAGA GGGATCCATG TCATCACC 28

( 2 ) INFORMATION FOR SEQ ID NO:82:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: cDNA viral ( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:

(B) CLONE:

(x) PUBLICATION INFORMATION:
(A) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
(B) TITLE: A Novel Hantavirus Associated with an Outbreak of Fatal Respiratory Disease in the Southwestern United States: Evolutionary Relationships to Known Hantaviruses- Running Title: Hantavirus-associated ARDS
(C) JOURNAL: Journal of Virology
(D) VOLUME: 68
(F) PAGES: in press
(G) DATE: 1994
(K) RELEVANT RESIDUES IN SEQ ID NO:1:FROM 1 TO 33

(xi) SEQUENCE DESCRIPTION: SEQ ID NO:82:

TACTACAGTC GACGGGATGA GCCAACTCAG GGA 33

(2) INFORMATION FOR SEQ ID NO:83:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: cDNA viral (iii) HYPOTHETICAL: no (iv) ANTI-SENSE: no (v) ORIGINAL SOURCE:
(A) ORGANISM: Four Corners Hantavirus
(C) INDIVIDUAL ISOLATE: 3H226

(vii) IMMEDIATE SOURCE:
(A) LIBRARY:
(B) CLONE:

(x) PUBLICATION INFORMATION:
(A) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
(B) TITLE: A Novel Hantavirus Associated with an Outbreak of Fatal Respiratory Disease in the Southwestern United States: Evolutionary Relationships to Known Hantaviruses- Running Title: Hantavirus-associated ARDS
(C) JOURNAL: Journal of Virology
(D) VOLUME: 68
(F) PAGES: in press
(G) DATE: 1994
(K) RELEVANT RESIDUES IN SEQ ID NO:1:FROM 1 TO 33

(xi) SEQUENCE DESCRIPTION: SEQ ID NO:83:

TGGTTCCTCG AGGTCAATGG AATTTACATC AAG 33

(2) INFORMATION FOR SEQ ID NO:84:

(i) SEQUENCE CHARACTERISTICS:
(A) LENGTH: 31
(B) TYPE: amino acid
(C) STRANDEDNESS: single
(D) TOPOLOGY: linear ( i i ) MOLECULE TYPE:

( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology
( D ) VOLUME: 68
( F ) PAGES: in press
( G ) DATE: 1994
( K ) RELEVANT RESIDUES IN SEQ ID NO:1:FROM 1 TO 31

( x i ) SEQUENCE DESCRIPTION: SEQ ID NO:84:

Leu Lys Leu Glu Ser Ser Cys Asn Phe Asp Val His Thr Ser Ser
5 10 15

Ala Thr Gln Gln Ala Val Thr Lys Trp Thr Trp Glu Lys Lys Ala
20 25 30

Asp ( 2 ) INFORMATION FOR SEQ ID NO:85:

( i ) SEQUENCE CHARACTERISTICS:
( A ) LENGTH: 31
( B ) TYPE: amino acid
( C ) STRANDEDNESS: single
( D ) TOPOLOGY: linear ( i i ) MOLECULE TYPE:

( i i i ) HYPOTHETICAL: no ( i v ) ANTI-SENSE: no ( v ) ORIGINAL SOURCE:
( A ) ORGANISM: Four Corners Hantavirus
( C ) INDIVIDUAL ISOLATE: 3H226

( v i i ) IMMEDIATE SOURCE:
( A ) LIBRARY:
( B ) CLONE:

( x ) PUBLICATION INFORMATION:
( A ) AUTHORS: Hjelle, Brian
Jenison, Steven
Torrez- Martinez, Norah
Yamada, Takashi
Nolte, Kurt
Zumwalt, Ross
MacInnes, Kersti
Myers, Gerald
( B ) TITLE: A Novel Hantavirus Associated with an Outbreak of Fatal Respiratory Disease in the Southwestern United States: Evolutionary Relationships to Known Hantaviruses- Running Title: Hantavirus-associated ARDS
( C ) JOURNAL: Journal of Virology -continued ( D ) VOLUME: 68
( F ) PAGES: in press
( G ) DATE: 1994
( K ) RELEVANT RESIDUES IN SEQ ID NO:1:FROM 1 TO 31

( x i ) SEQUENCE DESCRIPTION: SEQ ID NO:85:

```
Leu Lys Leu Glu Ser Ser Cys Asn Phe Asp Leu His Thr Ser Thr
                 5                  10                  15

Ala Gly Gln Gln Ser Phe Thr Lys Trp Thr Trp Glu Ile Lys Gly
                20                  25                  30

Asp
```

What is claimed is:

1. A purified antigenic protein encoded by an RNA nucleotide sequence or a DNA copy (cDNA) thereof of the Hantavirus Associated Respiratory Distress Syndrome (HARDS) virus genome M or S segments, wherein said protein is encoded by the coding sequence of the M segment according to SEQ. ID NO:23, or is an antigenic portion of said M segment, or is encoded by the coding sequence of the S segment according to SEQ. ID NO:20, or is an antigenic polypeptide portion of said S segment.

2. The antigenic portion of said M segment of claim 1, encoded by a DNA copy of the G1 or G2 glycoprotein coding sequence of the HARDS virus M segment, or an antigenic polypeptide portion of said G1 or G2 glycoprotein.

3. The antigenic portion of said S segment of claim 1, encoded by a DNA copy of the nucleocapsid (N) protein coding sequence of the HARDS virus S segment, or an antigenic portion of said N protein.

4. The antigenic portion of said N protein of claim 3, subtended by amino acids 1 and 4097, referenced to the amino acid sequence of PHV, which is cross-reactive with antisera to HARDS virus and at least one other hantavirus.

5. The antigenic portion of said N protein of claim 3, subtended by amino acids 1 and 322, referenced to the amino acid sequence of PHV.

6. The antigenic portion of said N protein of claim 3, subtended by amino acids 155 and 321, referenced to the amino acid sequence of PHV.

7. The antigenic portion of said N protein of claim 3, comprising an immunodominant cross-reactive epitope of HARDS virus N protein, wherein said antigenic portion is subtended by amino acids 1 and 100, referenced to the amino acid sequence of PHV.

8. The antigenic portion of said N protein of claim 3, subtended by amino acids 17 and 110.

9. The antigenic portion of said N protein of claim 3, wherein the N protein nucleotide coding sequence encodes the amino acid sequence MSTLKEVQDNITL-HEQQLVTARQKLKDAERAVELDPDDVNK-STLQSRRAAVSALETKLGELKRELADLIA according to SEQ. ID NO:10.

10. The antigenic portion of said N protein of claim 3, wherein the N protein nucleotide coding sequence encodes the amino acid sequence QLVTARQKLKDAERAVELDP-DDVNKSTLQSRRAAVSALETKLG according to SEQ. ID NO:17.

11. A purified antigenic protein according to claim 1, encoded by a cDNA nucleotide sequence.

12. The protein according to claim 11, expressed by one of clones p3H226-G1-1275-CR-1, p3H226-S-1229-pATH-1, p3H226-M-1225-CR-1, or p3H226-S-1129-CR-7.

13. The antigenic protein of claim 2, encoded by the glycoprotein G1 coding sequence, or an antigenic portion of said glycoprotein G1.

14. The antigenic portion of said glycoprotein G1 of claim 7, which has the amino acid sequence LKIESSCNFDLHV-PATTTQKYNQVDWTKKSS according to SEQ. ID NO: 9.

15. The antigenic portion of said glycoprotein G1 of claim 13, which has the amino acid sequence SCNFDLHV-PATTTQKYNQVDWTKKSS according to SEQ. ID NO:10, or an antigenic portion thereof.

16. The antigenic portion of said glycoprotein G1 of claim 13, comprising an immunodominant HARDS virus type-specific epitope.

17. An immunoassay for detecting human antibodies to HARDS virus, comprising contacting a tissue or blood sample with the antigenic portion of glycoprotein G1 according to claim 16 and screening the resulting product for antigen/antibody complex.

18. The antigenic portion of said glycoprotein G1 of claim 16, which is subtended by amino acids 59 and 89, referenced to the amino acid sequence of Prospect Hill virus (PHV).

19. An immunoassay for detecting human antibodies to HARDS virus, comprising contacting a tissue or blood sample with the antigenic portion of glycoprotein G1 according to claim 18 and screening the product for antigen/antibody complex.

20. A diagnostic kit for the detection of HARDS virus in vitro comprising a diagnostic amount of a HARDS virus antigenic protein or antigenic portion thereof of claim 1 as diagnostic immunoreagent.

21. The diagnostic kit of claim 20, wherein the immunoreagent is labelled to promote detection of immunoproduct comprising an antigen/antibody complex.

22. The protein or antigenic portion thereof according to any one of claims 1–3, 4–8, 11, 13, 16 or 18, which is reactive with human antibodies to the HARDS virus.

23. The protein or antigenic protein thereof according to one of claims 1–3, 4–8, 11, 13, 16 and 18, expressed by a molecular clone comprising a HARDS virus DNA oligonucleotide coding sequence encoding for the corresponding protein or antigenic portion thereof, cloned into an expression vector.

24. The protein or antigenic portion thereof according to one of claims 1–3, 4–8, 11, 13, 16 and 18, expressed by a host cell containing a DNA insert comprising a HARDS viral cDNA oligonucleotide coding sequence encoding for the corresponding protein or antigenic portion thereof ligated to an expression vector.

25. An immunoassay for detecting human antibodies to hantavirus infection comprising contacting a blood or tissue sample with a combination of at least three antigens including at least one type-specific antigen of the HARDS virus and at least one antigen of the HARDS virus cross-reactive with antisera to at least one other hantavirus, and screening the resulting product for antibody/antigen complex.

26. The immunoassay of claim 25, wherein the combination of at least three antigens comprises the antigenic portion of glycoprotein G1 subtended by amino acids 59 and 89, the antigenic portion of the N protein subtended by amino acids 155 and 321, and the antigenic portion of the N protein subtended by amino acids 1 and 100, all referenced to the amino acid sequence of PHV.

27. The immunoassay of claim 25, wherein the antigens comprise the products of clones p3H226-G1-1275-CR-1, p3H226-S-1229-pATH-1, p3H226-M-1225-CR-1, or p3H226-S-1129-CR-7.

28. The immunoassay of claim 17 or 25 which is a western blot immunoassay.

29. The immunoassay of claim 17 or 25 which is an enzyme-linked immunoassay.

* * * * *